(12) United States Patent
Barnes

(10) Patent No.: US 11,839,532 B2
(45) Date of Patent: Dec. 12, 2023

(54) ABSORBENT ARTICLE WITH PARTIALLY ENCLOSED WAIST CONTAINMENT MEMBER AND METHOD OF MANUFACTURING THEREOF

(71) Applicant: Kimberly-Clark Worldwide, Inc., Neenah, WI (US)

(72) Inventor: Nickolas Barnes, Menasha, WI (US)

(73) Assignee: KIMBERLY-CLARK WORLDWIDE, INC., Neenah, WI (US)

(*) Notice: Subject to any disclaimer, the term of this patent is extended or adjusted under 35 U.S.C. 154(b) by 1407 days.

(21) Appl. No.: 16/193,680

(22) Filed: Nov. 16, 2018

(65) Prior Publication Data

US 2019/0083331 A1     Mar. 21, 2019

Related U.S. Application Data

(62) Division of application No. 15/507,811, filed as application No. PCT/US2015/038271 on Jun. 29, 2015, now Pat. No. 10,159,610.

(51) Int. Cl.
    *A61F 13/53*      (2006.01)
    *A61F 13/49*      (2006.01)
    (Continued)

(52) U.S. Cl.
    CPC ........ *A61F 13/53* (2013.01); *A61F 13/15585* (2013.01); *A61F 13/15699* (2013.01);
    (Continued)

(58) Field of Classification Search
CPC ............ A61F 13/5585; A61F 13/15699; A61F 13/49466; A61F 13/15723; A61F 13/15747
See application file for complete search history.

(56) References Cited

U.S. PATENT DOCUMENTS 3,395,708 A    8/1968   George et al.
3,800,796 A    4/1974   Jacob et al.
(Continued)

FOREIGN PATENT DOCUMENTS

CN      1200662 C    5/2005
CN      1853592 A    11/2006
(Continued)

*Primary Examiner* — Carson Gross
(74) *Attorney, Agent, or Firm* — KIMBERLY-CLARK WORLDWIDE, INC.

(57) ABSTRACT

An absorbent article (10, 110) can include a waist containment member (54) with a first longitudinal side edge (72), a second longitudinal side edge (74), a proximal portion (76), an intermediate portion (77), and a distal portion (78). The proximal portion (76) can be coupled to the chassis (11) of the absorbent article (10, 110). The intermediate portion (77) can be free to move independent of the proximal portion (76) and the distal portion (78) and free to move independent of the body facing surface (19) of the chassis (11) to provide a containment pocket (82) for containing body exudates. The distal portion (78) can be disposed underneath the intermediate portion (77) when the absorbent article (10, 110) is in the stretched, laid-flat configuration. The waist containment member (54) can also include a first lateral tack-down region (83*a*) and a second lateral tack-down region (83*b*).

8 Claims, 10 Drawing Sheets

(51) Int. Cl.
  *A61F 13/494* (2006.01)
  *A61F 13/15* (2006.01)
  *A61F 13/496* (2006.01)

(52) U.S. Cl.
  CPC .. *A61F 13/15723* (2013.01); *A61F 13/15747* (2013.01); *A61F 13/15804* (2013.01); *A61F 13/49001* (2013.01); *A61F 13/496* (2013.01); *A61F 13/49011* (2013.01); *A61F 13/4942* (2013.01); *A61F 13/49466* (2013.01); *A61F 2013/49092* (2013.01); *A61F 2013/530481* (2013.01)

(56) References Cited

U.S. PATENT DOCUMENTS

| | | | |
|---|---|---|---|
| 3,848,594 A | 11/1974 | Buell et al. | |
| 3,860,003 A | 1/1975 | Buell | |
| 3,930,501 A | 1/1976 | Schaar | |
| 3,978,861 A | 9/1976 | Schaar | |
| 3,995,640 A | 12/1976 | Schaar | |
| 4,074,716 A | 2/1978 | Schaar | |
| 4,525,407 A | 6/1985 | Ness | |
| 4,642,110 A | 2/1987 | Dudek | |
| 4,643,729 A | 2/1987 | Laplanche | |
| 4,657,539 A | 4/1987 | Hasse | |
| 4,657,802 A | 4/1987 | Morman | |
| 4,681,579 A | 7/1987 | Toussant et al. | |
| 4,735,624 A | 4/1988 | Mazars | |
| 4,738,677 A | 4/1988 | Foreman | |
| 4,741,949 A | 5/1988 | Morman et al. | |
| 4,753,646 A | 6/1988 | Enloe | |
| 4,808,176 A | 2/1989 | Kielpikowski | |
| 4,808,177 A | 2/1989 | DesMarais et al. | |
| 4,822,435 A | 4/1989 | Igaue et al. | |
| 4,850,990 A | 7/1989 | Huntoon et al. | |
| 4,935,021 A | 6/1990 | Huffman et al. | |
| 4,938,755 A | 7/1990 | Foreman | |
| 4,977,011 A | 12/1990 | Smith | |
| 5,026,364 A | 6/1991 | Robertson | |
| 5,064,421 A | 11/1991 | Tracy | |
| 5,069,672 A | 12/1991 | Wippler et al. | |
| 5,106,385 A | 4/1992 | Allen et al. | |
| 5,151,091 A | 9/1992 | Glaug et al. | |
| 5,151,092 A | 9/1992 | Buell et al. | |
| 5,187,817 A | 2/1993 | Zolner | |
| 5,209,801 A | 5/1993 | Smith | |
| 5,366,452 A | 11/1994 | Widlund et al. | |
| 5,397,318 A | 3/1995 | Dreier | |
| 5,413,570 A | 5/1995 | Enloe | |
| 5,439,459 A | 8/1995 | Tanji et al. | |
| 5,451,219 A | 9/1995 | Suzuki et al. | |
| 5,514,104 A | 5/1996 | Cole et al. | |
| 5,514,121 A | 5/1996 | Roe et al. | |
| 5,531,730 A | 7/1996 | Dreier | |
| 5,540,671 A | 7/1996 | Dreier | |
| 5,558,660 A | 9/1996 | Dreier | |
| 5,558,661 A | 9/1996 | Roe et al. | |
| 5,569,227 A | 10/1996 | Vandemoortele et al. | |
| 5,582,606 A | 12/1996 | Bruemmer et al. | |
| 5,593,401 A | 1/1997 | Sosalla et al. | |
| 5,624,422 A | 4/1997 | Allen | |
| 5,643,242 A | 7/1997 | Lavon et al. | |
| 5,649,918 A | 7/1997 | Schleinz | |
| 5,667,503 A | 9/1997 | Roe et al. | |
| 5,672,166 A | 9/1997 | Vandemoortele | |
| 5,674,215 A | 10/1997 | Ronnberg | |
| 5,685,873 A | 11/1997 | Bruemmer | |
| 5,690,627 A | 11/1997 | Clear et al. | |
| 5,695,488 A | 12/1997 | Sosalla | |
| 5,776,121 A | 7/1998 | Roe et al. | |
| 5,795,347 A | 8/1998 | Roe et al. | |
| 5,817,086 A | 10/1998 | Kling | |
| 5,827,259 A | 10/1998 | Laux et al. | |
| 5,858,012 A | 1/1999 | Yamaki et al. | |
| 5,895,382 A | 4/1999 | Popp et al. | |
| 5,904,675 A | 5/1999 | Laux et al. | |
| 5,931,826 A | 8/1999 | Faulks et al. | |
| 5,938,652 A | 8/1999 | Sauer | |
| 5,993,433 A | 11/1999 | St. Louis et al. | |
| 6,103,952 A | 8/2000 | Coles et al. | |
| 6,132,410 A | 10/2000 | Van Gompel et al. | |
| 6,135,988 A | 10/2000 | Turner et al. | |
| 6,142,985 A | 11/2000 | Feist | |
| 6,149,638 A | 11/2000 | Vogt et al. | |
| 6,174,303 B1 | 1/2001 | Suprise et al. | |
| 6,217,563 B1 | 4/2001 | Van Gompel et al. | |
| 6,258,076 B1 | 7/2001 | Glaug et al. | |
| 6,264,639 B1 | 7/2001 | Sauer | |
| 6,264,641 B1 | 7/2001 | Van Gompel et al. | |
| 6,280,426 B1 | 8/2001 | Turner et al. | |
| 6,293,937 B2 | 9/2001 | Matsushita et al. | |
| 6,306,122 B1 | 10/2001 | Narawa et al. | |
| 6,315,764 B1 | 11/2001 | Faulks et al. | |
| 6,425,889 B1 | 7/2002 | Kitaoka et al. | |
| 6,443,933 B1 | 9/2002 | Suzuki et al. | |
| 6,455,753 B1 | 9/2002 | Glaug et al. | |
| 6,458,114 B1 | 10/2002 | Mishima et al. | |
| 6,482,194 B1 | 11/2002 | Putzer | |
| 6,491,677 B1 | 12/2002 | Glaug et al. | |
| 6,494,872 B1 | 12/2002 | Suzuki et al. | |
| 6,506,185 B1 | 1/2003 | Sauer et al. | |
| 6,527,756 B1 | 3/2003 | Mishima et al. | |
| 6,638,262 B2 | 10/2003 | Suzuki et al. | |
| 6,648,870 B2 | 11/2003 | Itoh et al. | |
| 6,699,228 B1 | 3/2004 | Chmielewski et al. | |
| 6,827,806 B2 | 12/2004 | Uitenbroek et al. | |
| 6,838,591 B2 | 1/2005 | Waksmundzki et al. | |
| 6,881,207 B1 | 4/2005 | Tracy | |
| 6,890,327 B2 | 5/2005 | Suzuki et al. | |
| 7,066,921 B2 | 6/2006 | Schmoker et al. | |
| 7,166,093 B2 | 1/2007 | Drevik et al. | |
| 7,166,095 B1 | 1/2007 | Coates | |
| 7,247,152 B2 | 7/2007 | Klemp et al. | |
| 7,604,625 B2 | 10/2009 | Turi et al. | |
| 7,666,173 B2 | 2/2010 | Mishima et al. | |
| 7,767,876 B2 | 8/2010 | Davis et al. | |
| 7,842,021 B2 | 11/2010 | Wood et al. | |
| 7,879,017 B1 | 2/2011 | Tabata et al. | |
| 7,993,314 B2 | 8/2011 | Asp et al. | |
| 8,075,543 B2 | 12/2011 | Okuda | |
| 9,044,359 B2 | 6/2015 | Wciorka et al. | |
| 10,010,458 B2 | 7/2018 | Barnes | |
| 2001/0016720 A1 | 8/2001 | Otsubo | |
| 2002/0045878 A1 | 4/2002 | Shimoe et al. | |
| 2002/0082570 A1 | 6/2002 | Mishima et al. | |
| 2002/0147438 A1 | 10/2002 | Tanaka et al. | |
| 2003/0045853 A1 | 3/2003 | Sauer | |
| 2003/0050616 A1 | 3/2003 | Reynolds et al. | |
| 2003/0109844 A1 | 6/2003 | Gibbs | |
| 2003/0119405 A1 | 6/2003 | Abuto et al. | |
| 2004/0002690 A1 | 1/2004 | Miyamoto | |
| 2004/0019343 A1 | 1/2004 | Olson et al. | |
| 2004/0127882 A1 | 7/2004 | Weber | |
| 2004/0243086 A1 | 12/2004 | VanGompel et al. | |
| 2005/0027274 A1 | 2/2005 | Suzuki et al. | |
| 2005/0148974 A1 | 7/2005 | Datta et al. | |
| 2005/0215974 A1 | 9/2005 | O'Connell | |
| 2005/0256488 A1 | 11/2005 | Sperl | |
| 2006/0058738 A1 | 3/2006 | Ponzi et al. | |
| 2006/0058767 A1 | 3/2006 | Zhang et al. | |
| 2007/0093164 A1 | 4/2007 | Nakaoka | |
| 2007/0112322 A1 | 5/2007 | Ashton et al. | |
| 2007/0255245 A1 | 11/2007 | Asp et al. | |
| 2007/0293832 A1 | 12/2007 | Wood et al. | |
| 2008/0300560 A1 | 12/2008 | Magnusson et al. | |
| 2010/0305533 A1 | 12/2010 | Ashton et al. | |
| 2012/0277703 A1 | 11/2012 | Rhein et al. | |
| 2012/0323207 A1 | 12/2012 | Takaishi | |
| 2013/0012905 A1 | 1/2013 | Katsuragawa et al. | |
| 2013/0012906 A1 | 1/2013 | Takino | |
| 2013/0012907 A1 | 1/2013 | Sasayama et al. | |
| 2013/0046266 A1 | 2/2013 | Kawakami | |
| 2014/0018761 A1 | 1/2014 | Orchard, IV et al. | |

(56) References Cited

U.S. PATENT DOCUMENTS

| | | |
|---|---|---|
| 2014/0121623 A1 | 5/2014 | Kirby et al. |
| 2014/0128829 A1 | 5/2014 | Miyake et al. |
| 2014/0257231 A1 | 9/2014 | Wang et al. |
| 2014/0350504 A1 | 11/2014 | Popp et al. |
| 2015/0051568 A1 | 2/2015 | Sakaguchi et al. |
| 2015/0182388 A1 | 7/2015 | Katsuragawa et al. |
| 2017/0000658 A1 | 1/2017 | Chatterjee et al. |
| 2017/0128281 A1 | 5/2017 | Takino et al. |
| 2017/0239104 A1 | 8/2017 | Jang et al. |
| 2017/0246054 A1 | 8/2017 | Bishop et al. |
| 2017/0246055 A1 | 8/2017 | Barnes |
| 2017/0296401 A1 | 10/2017 | Sugiyama et al. |
| 2018/0055698 A1 | 3/2018 | Bishop et al. |
| 2018/0071155 A1 | 3/2018 | Bishop et al. |
| 2018/0104116 A1 | 4/2018 | Bishop et al. |

FOREIGN PATENT DOCUMENTS

| | | |
|---|---|---|
| CN | 102065811 A | 5/2011 |
| CN | 102065813 B | 11/2014 |
| CN | 204072501 U | 1/2015 |
| JP | 2001178772 A2 | 7/2001 |
| JP | 4754634 B2 | 8/2011 |
| KR | 100648562 B1 | 11/2006 |
| KR | 2020130001181 U | 2/2013 |
| WO | 9601607 A1 | 1/1996 |
| WO | WO0037008 A1 | 6/2000 |
| WO | 13021897 A1 | 2/2013 |
| WO | WO2016159983 A1 | 10/2016 |

ABSORBENT ARTICLE WITH PARTIALLY ENCLOSED WAIST CONTAINMENT MEMBER AND METHOD OF MANUFACTURING THEREOF

RELATED APPLICATIONS

The present application is a divisional application and claims priority to U.S. patent application Ser. No. 15/507,811, filed on Mar. 1, 2017, which is a national-phase entry, under 35 U.S.C. § 371, of PCT Patent Application No. PCT/US15/38271, filed on Jun. 29, 2015 all of which are incorporated herein by reference.

TECHNICAL FIELD

The present disclosure relates to absorbent articles.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

One common mode of failure is for exudates to leak out of the rear waist region or the front waist region of an absorbent article. As one example, fecal material that is not absorbed or contained by the absorbent article can move past the gaps between the absorbent article and the wearer's skin in the rear waist region and soil or contaminate the wearer's skin and clothing near their back. This may be more common of an occurrence for semi-solid fecal material, such as low viscosity fecal material, which can be prevalent with younger children. Such exudates can move around on the bodyside liner of an absorbent article under the influence of gravity, motion, force, and pressure by the wearer of the absorbent article. In such a circumstance, not only does the wearer's absorbent article need to be changed, but the wearer's clothing and/or bedding often also needs to be changed, resulting in additional work, expense, and stress for the caregiver.

Attempts have been made in the past to provide containment systems, especially on the bodyside liner or near the rear waist region to solve the problems described above. One example is by providing a waist elastic member and not adhering a portion of the waist containment member closest to the lateral axis of the absorbent article to the bodyside liner, such that the non-adhered portion of the waist elastic member can provide a containment pocket for exudates. One example of this configuration is a HUGGIES® Little Snugglers diaper. Although absorbent articles with such containment members intend to prevent leakage of exudates and have functioned adequately, failures can still occur.

Thus, there is a desire for improvements to containment systems and containment members of absorbent articles to prevent leakage of exudates, especially in the waist regions of the absorbent article. There is also a desire for improvements in containment systems to have increased void volumes to hold body exudates until the absorbent article can be changed.

SUMMARY OF THE DISCLOSURE

In one embodiment, an absorbent article can include a front waist region, a rear waist region, a crotch region, a longitudinal axis and a lateral axis. The absorbent article can include a chassis including an absorbent body. The chassis can include a body facing surface and a garment facing surface. The absorbent article can also include a waist containment member disposed on the body facing surface of the chassis. The waist containment member can include a first longitudinal side edge and a second longitudinal side edge. The first longitudinal side edge can be disposed on a first side of the longitudinal axis and the second longitudinal edge can be disposed on a second side of the longitudinal axis. The waist containment member can further include an upper lateral edge and a lower lateral edge. The first longitudinal side edge, the second longitudinal side edge, the upper lateral edge, and the lower lateral edge of the waist containment member can be defined when the absorbent article is in a stretched laid-flat configuration. The waist containment member can also include a proximal portion that can be coupled to the body facing surface of the chassis. The waist containment member can further include a distal portion and an intermediate portion. The intermediate portion can be disposed between the proximal portion and the distal portion. The intermediate portion can be free to move independent of the proximal portion and the distal portion and can be free to move independent of the body facing surface of the chassis to provide a containment pocket for containing body exudates. The distal portion can be disposed underneath the intermediate portion when the absorbent article is in the stretched laid-flat configuration.

In another embodiment, an absorbent article can include a front waist region, a rear waist region, a crotch region, a longitudinal axis and a lateral axis. The absorbent article can include a chassis including an absorbent body. The chassis can include a body facing surface and a garment facing surface. The absorbent article can also include a waist containment member disposed on the body facing surface of the chassis. The waist containment member can include a first longitudinal side edge and a second longitudinal side edge. The first longitudinal side edge can be disposed on a first side of the longitudinal axis and the second longitudinal edge can be disposed on a second side of the longitudinal axis. The waist containment member can further include an upper lateral edge and a lower lateral edge. The first longitudinal side edge, the second longitudinal side edge, the upper lateral edge, and the lower lateral edge of the waist containment member can be defined when the absorbent article is in a stretched laid-flat configuration. The waist containment member can also include a proximal portion that can be coupled to the body facing surface of the chassis. The waist containment member can further include a distal portion. The waist containment member can additionally include a first lateral tack-down region and a second lateral tack-down region. The first lateral tack-down region can include the distal portion of the waist containment member on the first side of the longitudinal axis being coupled to the body facing surface of the chassis from the first longitudinal side edge in a lateral direction towards the proximal end of the base portion of the first containment flap. The second lateral tack-down region can include the distal portion of the waist containment member on the second side of the longitudinal axis being coupled to the body facing surface of the chassis from the second longitudinal side edge in a lateral direction towards the proximal end of the base portion of the second containment flap. The waist containment member can be gathered in the longitudinal direction such that the waist containment member can extend away from the body facing surface of the chassis to provide a containment pocket for containing exudates between the first lateral tack-down region and the upper lateral edge of the waist containment member and between the second lateral tack-down region and the upper lateral edge of the waist containment member.

In yet another embodiment, a method of manufacturing an absorbent article is provided. The absorbent article can include a front waist region, a rear waist region, a crotch region, a longitudinal axis and a lateral axis. The method can include providing a chassis including a body facing surface. The chassis can include an absorbent assembly including a bodyside liner, an outer cover, and an absorbent body disposed between the bodyside liner and the outer cover. The absorbent assembly can include a body facing surface. The method can further include providing a continuous web of waist containment member material. The method can also include folding at least a first portion of the continuous web of waist containment member material upon itself to provide a folded edge. The method can additionally include cutting the continuous web of waist containment member material to provide a waist containment member including a proximal portion, an intermediate portion, a distal portion, a first longitudinal side edge, a second longitudinal side edge, an upper lateral edge, and a lower lateral edge. The folded edge can provide the distal portion to be folded against the intermediate portion and can define the lower lateral edge of the waist containment member. The intermediate portion can be disposed between the proximal portion and the distal portion. The method can also include bonding the proximal portion of the waist containment member to the body facing surface of the chassis. The method can include bonding the distal portion of the waist containment member to the body facing surface of the chassis to provide a first lateral tack-down region near the first longitudinal side edge of the waist containment member and a second lateral tack-down region near the second longitudinal side edge of the waist containment member. The first lateral tack-down region and the second lateral tack-down region can be formed such that the first lateral tack-down region and the second lateral tack-down region of the waist containment member are disposed away from the lower lateral edge of the waist containment member when the absorbent article is in the stretched laid-flat configuration.

BRIEF DESCRIPTION OF DRAWINGS

A full and enabling disclosure thereof, directed to one of ordinary skill in the art, is set forth more particularly in the remainder of the specification, which makes reference to the appended figures in which.

Figure 1:
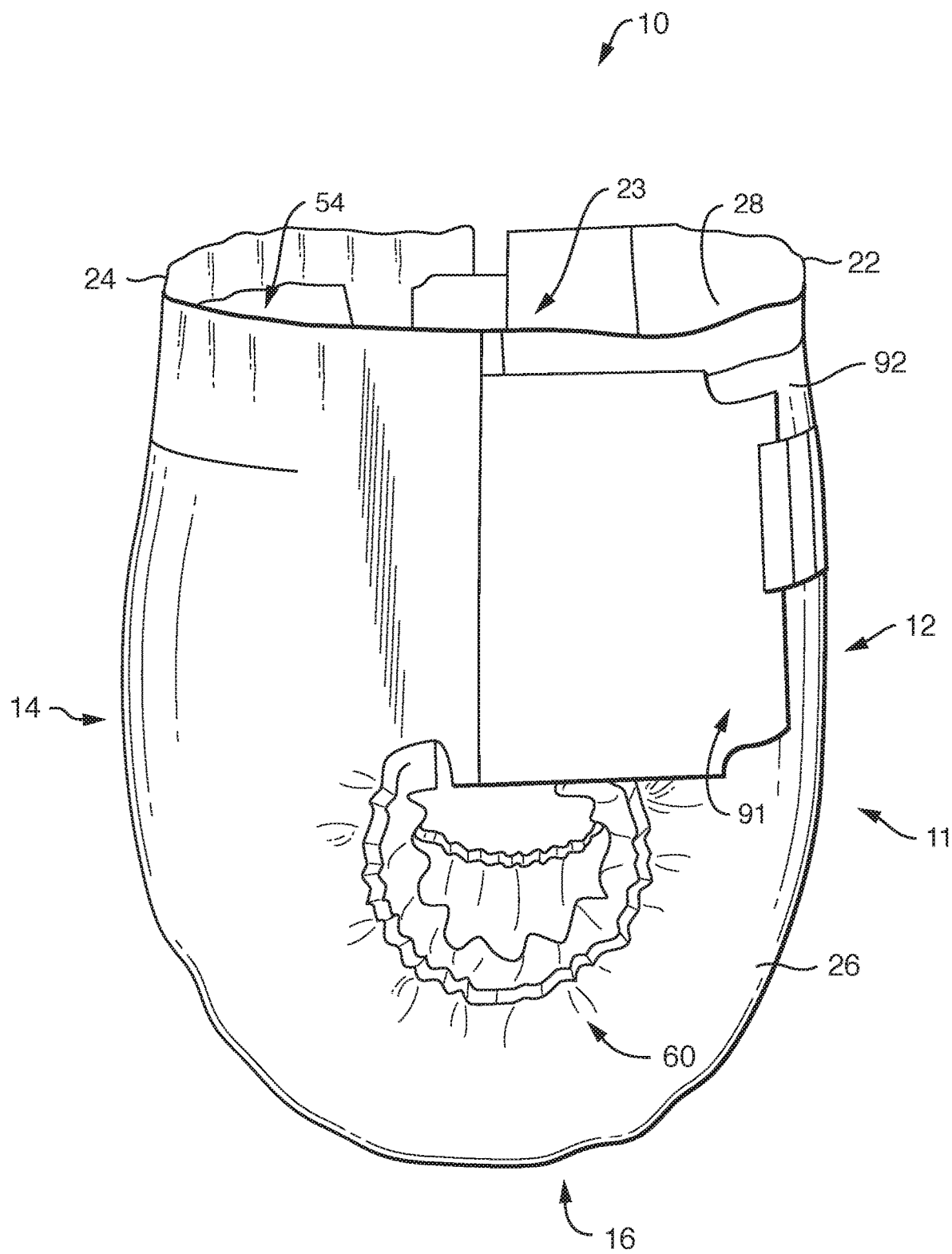
FIG. 1 is side perspective view of an exemplary embodiment of an absorbent article, such as a diaper, in a fastened condition.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an absorbent article 10, 110 having a waist containment member 54, 154, 254, 354, 454, 554 providing volume for exudates and a method of manufacturing 610 thereof. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Absorbent Article:

Referring to FIGS. 1-5A, a non-limiting illustration of an absorbent article 10, for example, a diaper, is illustrated. Other embodiments of the absorbent article could include training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure. For example, the absorbent article 110 in FIGS. 6 and 7 provides an exemplary embodiment of an absorbent article 110 that can be manufactured in cross-direction manufacturing process.

Figure 2:
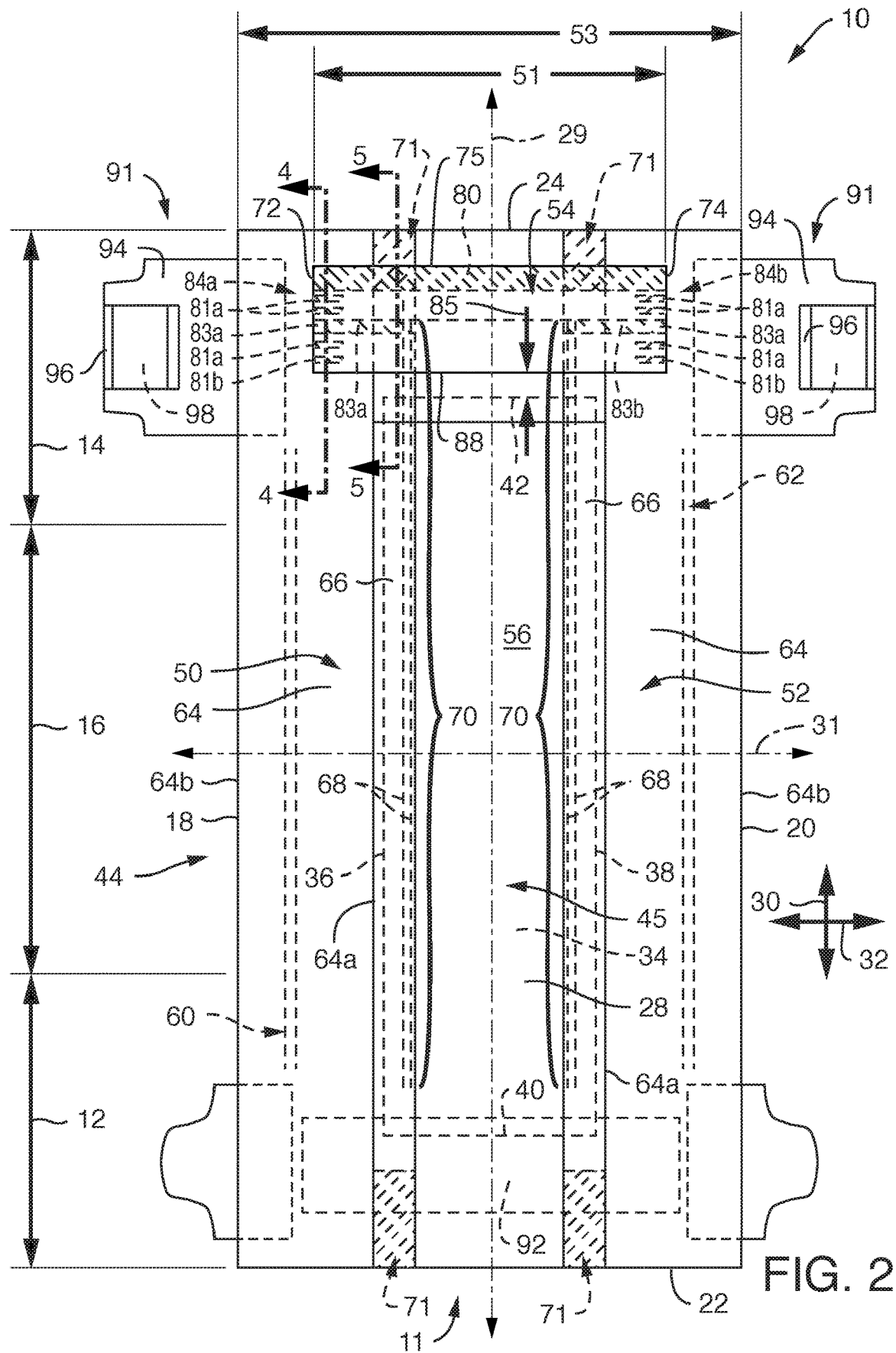
FIG. 2 is a top plan view of the absorbent article of FIG. 1 in a stretched, laid flat, unfastened condition.
Figure 6:
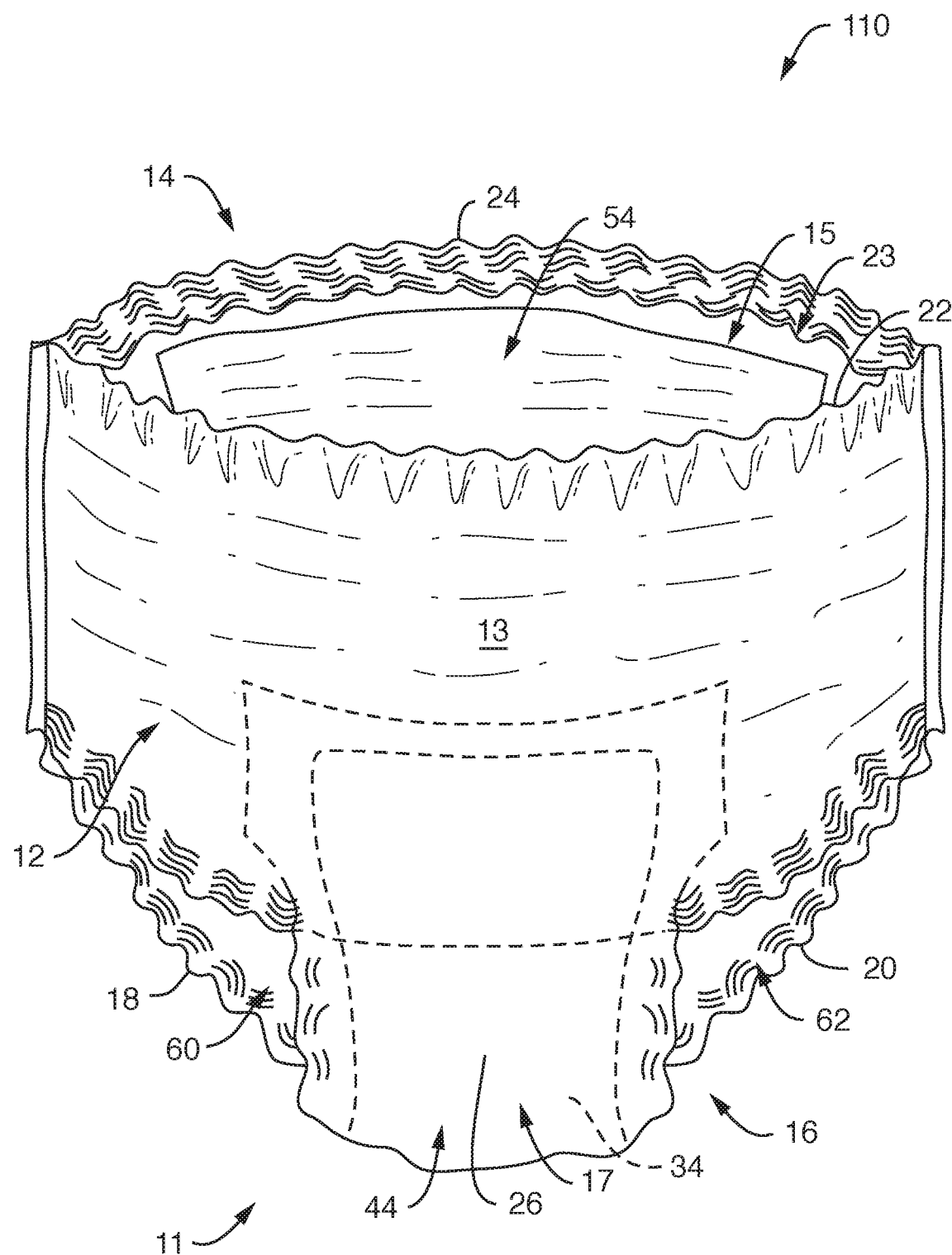
FIG. 6 is a front perspective view of an alternative embodiment of an absorbent article, such as a pant.
Figure 7:
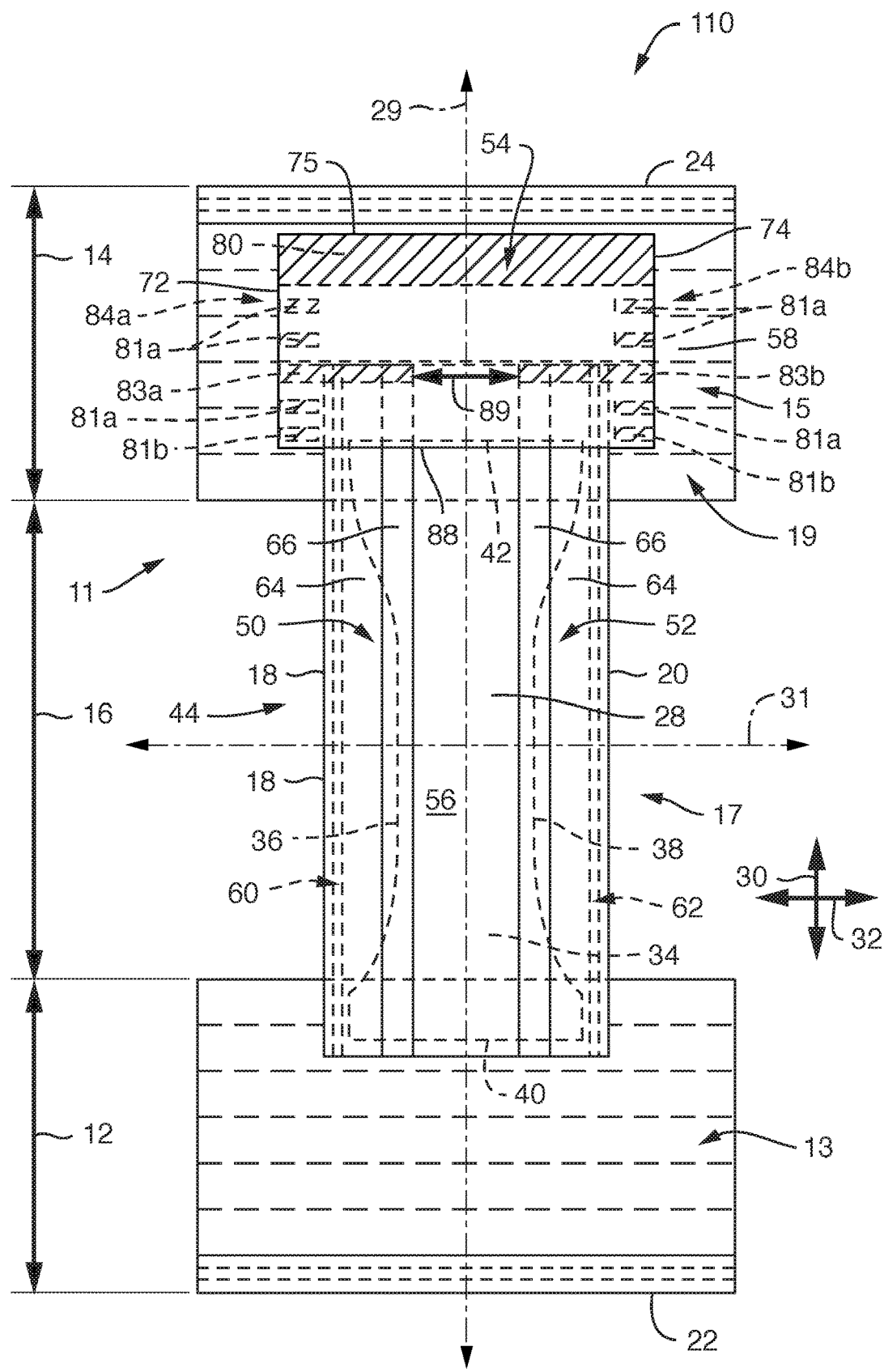
FIG. 7 is a top plan view of the absorbent article of FIG. 6 in a stretched, laid flat condition.

The absorbent article 10 illustrated in FIGS. 1 and 2 and the absorbent article 110 in FIGS. 6 and 7 can each include a chassis 11. The absorbent article 10, 110 can include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. In the embodiment depicted in FIGS. 6 and 7, a three-piece construction of an absorbent article 110 is depicted where the absorbent article 110 can have a chassis 11 including a front waist panel 13 defining the front waist region 12, a rear waist panel 15 defining the rear waist region 14, and an absorbent panel 17 defining the crotch region 16 of the absorbent article 110. The absorbent panel 17 can extend between the front waist panel 13 and the rear waist panel 15. In some embodiments, the absorbent panel 17 can overlap the front waist panel 13 and the rear waist panel 15. The absorbent panel 17 can be bonded to the front waist panel 13 and the rear waist panel 15 to define a three-piece construction. However, it is contemplated that an absorbent article can be manufactured in a cross-direction without being a three-piece construction garment.

The absorbent article 10, 110 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, such as for the absorbent articles 10, 110 illustrated in FIGS. 2 and 6. In other embodiments, the longitudinal side edges 18, 20 can be curved between the front waist edge 22 and the rear waist edge 24. In the absorbent article 110 of FIGS. 6 and 7, the longitudinal side edges 18, 20 can include portions of the front waist panel 13, the absorbent panel 17, and the rear waist panel 15.

The front waist region 12 can include the portion of the absorbent article 10, 110 that, when worn, is positioned at least in part on the front of the wearer while the rear waist region 14 can include the portion of the absorbent article 10, 110 that, when worn, is positioned at least in part on the back of the wearer. The crotch region 16 of the absorbent article 10, 110 can include the portion of the absorbent article 10, 110 that, when worn, is positioned between the legs of the wearer and can partially cover the lower torso of the wearer. The waist edges, 22 and 24, of the absorbent article 10, 110 are configured to encircle the waist of the wearer and together define a central waist opening 23 (as labeled in FIG. 1 and FIG. 6) for the waist of the wearer. Portions of the longitudinal side edges 18, 20 in the crotch region 16 can generally define leg openings for the legs of the wearer when the absorbent article 10, 110 is worn.

Figure 4:
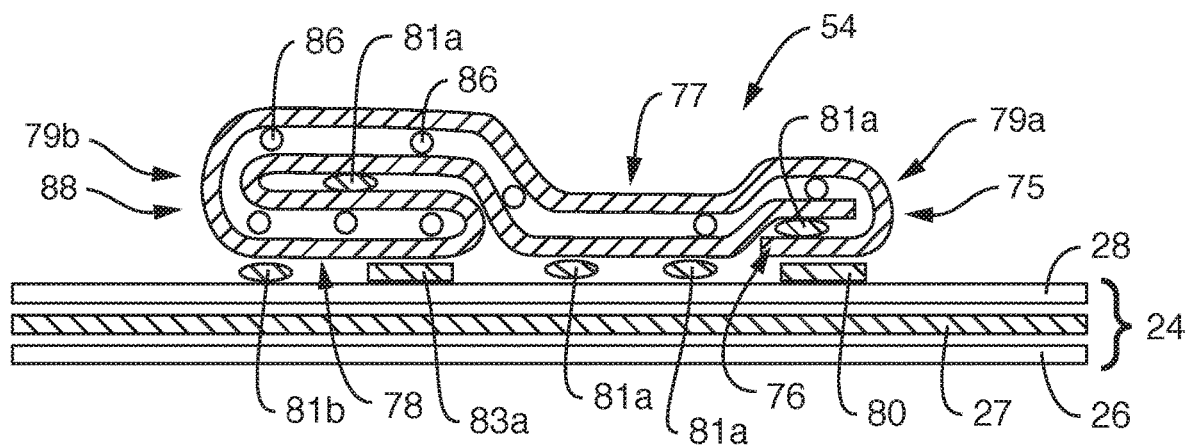
FIG. 4 is a cross-sectional view taken along line 4-4 from FIG. 2.
Figure 5A:
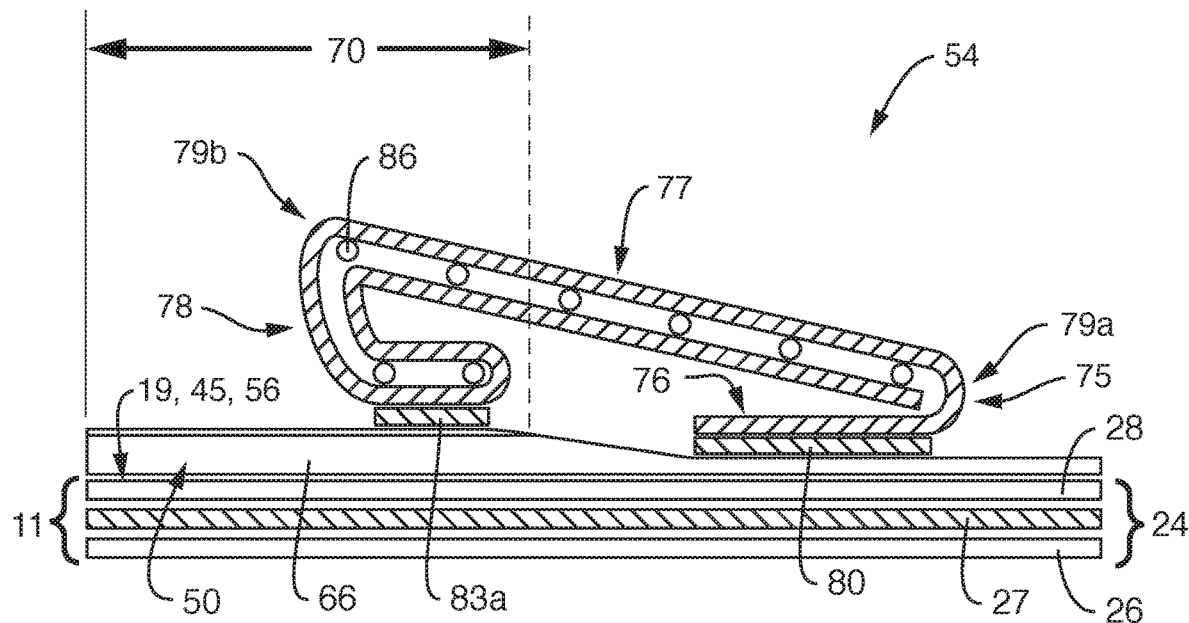
FIG. 5A is a cross-sectional view taken along line 5-5 from FIG. 2, but with the waist containment member being shown in a relaxed configuration such that the waist containment member can provide void volume for exudates.
Figure 5B:
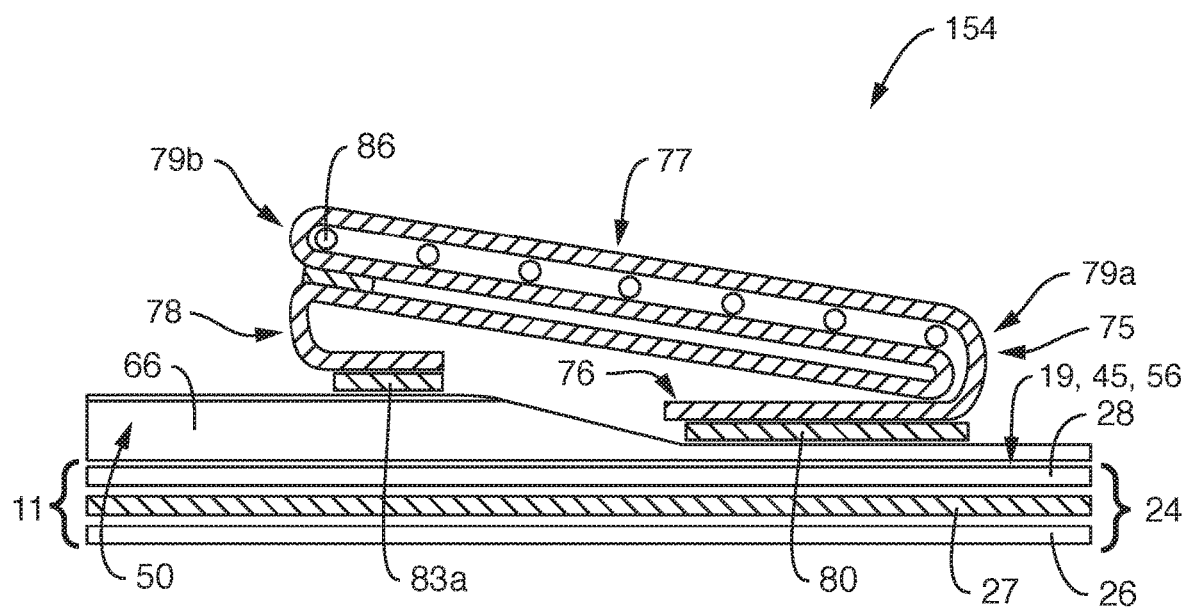
FIG. 5B is a cross-sectional view similar to FIG. 5A, but of an alternative embodiment of a waist containment member.
Figure 5C:
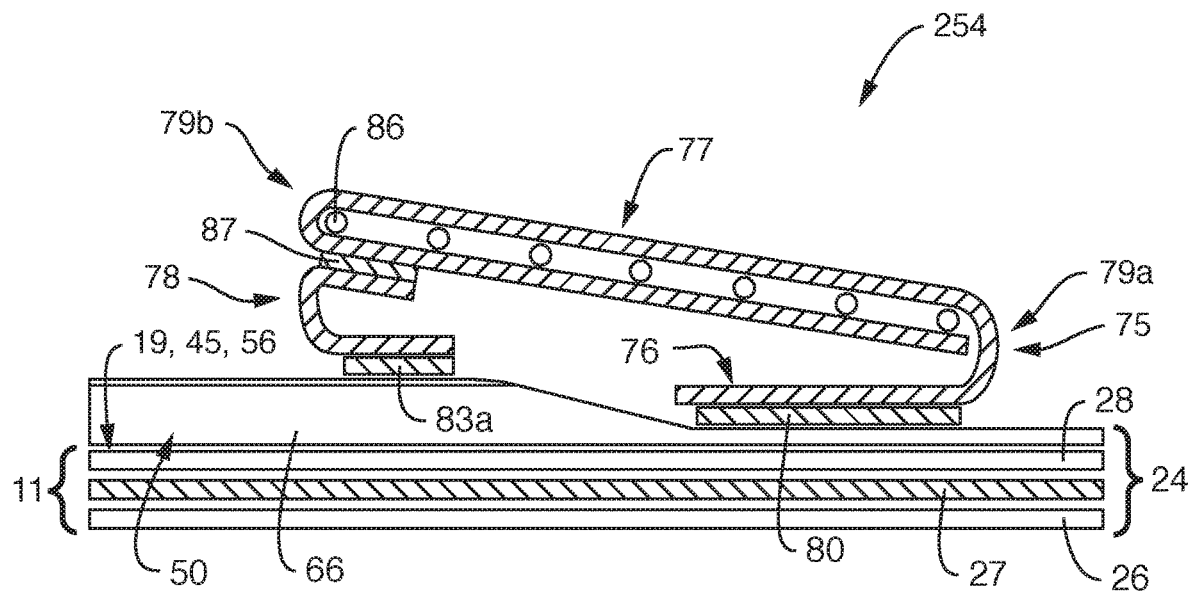
FIG. 5C is a cross-sectional view similar to FIG. 5A, but of an alternative embodiment of a waist containment member.
Figure 5D:
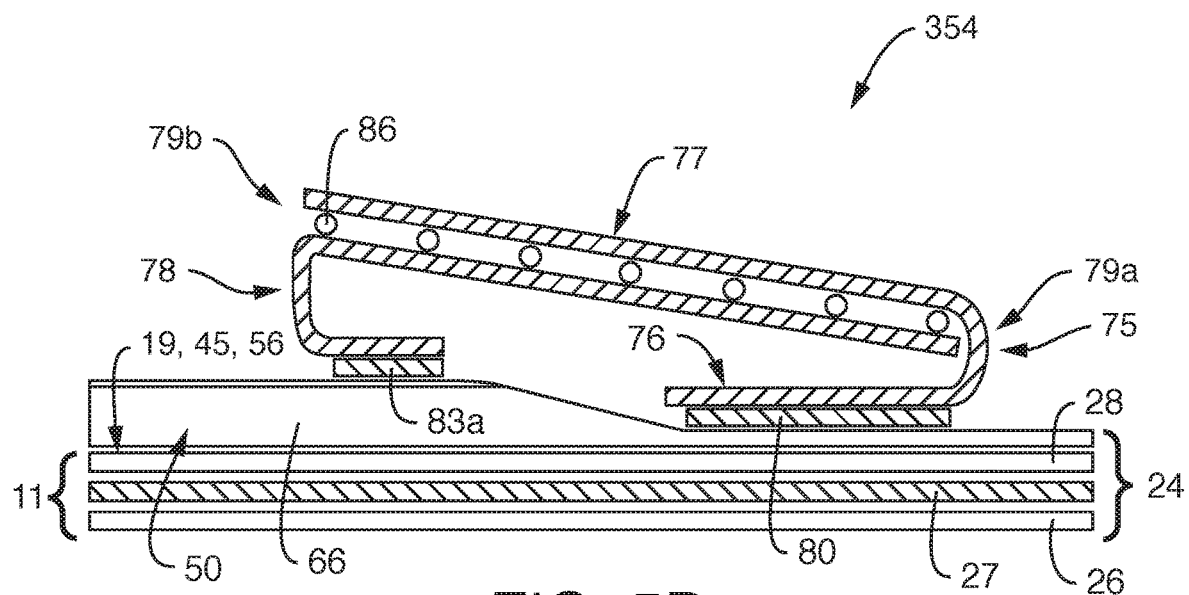
FIG. 5D is a cross-sectional view similar to FIG. 5A, but of an alternative embodiment of a waist containment member.

The absorbent article 10, 110 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. As an example, FIGS. 4-5F depict the bodyside liner 28 bonded to the outer cover 26 with adhesive 27. The outer cover 26 can define a length in a longitudinal direction 30, and a width in the lateral direction 32, which, in the illustrated embodiment, can coincide with the length and width of the absorbent article 10, 110. As illustrated in FIGS. 2 and 7, the absorbent article 10, 110 can have a longitudinal axis 29 extending in the longitudinal direction 30 and a lateral axis 31 extending in the lateral direction 32.

The chassis 11 can include an absorbent body 34. The absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10, 110. The absorbent body 34 can have a first end edge 40 that is opposite a second end edge 42, respectively, which, in an embodiment, can form portions of the waist edges, 22 and 24, respectively, of the absorbent article 10, 110. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent article 10, 110. The bodyside liner 28, the outer cover 26, and the absorbent body 34 can form part of an absorbent assembly 44. In the absorbent article 110 of FIGS. 6 and 7, the absorbent panel 17 can form the absorbent assembly 44. The absorbent assembly 44 can also include a fluid transfer layer (not shown) and a fluid acquisition layer (not shown) between the bodyside liner 28 and the fluid transfer layer as is known in the art. The absorbent assembly 44 can also include a spacer layer (not shown) disposed between the absorbent body 34 and the outer cover 26 as is known in the art.

The absorbent article 10, 110 can be configured to contain and/or absorb liquid, solid, and semi-solid body exudates discharged from the wearer. In some embodiments, containment flaps 50, 52 can be configured to provide a barrier to the lateral flow of body exudates. To further enhance containment and/or absorption of body exudates, the absorbent article 10, 110 can suitably include a waist containment member 54, 154, 254, 354, 454, 554. In some embodiments, the waist containment member 54, 154, 254, 354, 454, 554 can be disposed in the rear waist region 14 of the absorbent article 10, 110. Although not depicted herein, it is contemplated that the waist containment member 54, 154, 254, 354, 454, 554 can be additionally or alternatively disposed in the front waist region 12 of the absorbent article 10, 110.

The waist containment member 54, 154, 254, 354, 454, 554 can be disposed on the body facing surface 19 of the chassis 11 to help contain and/or absorb body exudates. In some embodiments, such as in the absorbent article 10 depicted in FIGS. 1-5F, the waist containment member 54, 154, 254, 354, 454, 554 can be disposed on the body facing surface 45 of the absorbent assembly 44. In some embodiments, the waist containment member 54, 154, 254, 354, 454, 554 can be disposed on the body facing surface 56 of the bodyside liner 28. In some embodiments, such as in the absorbent article 110 depicted in FIGS. 6 and 7, the waist containment member 54 can be disposed on the body facing surface 58 of the rear waist panel 15.

The absorbent article 10, 110 can further include leg elastic members 60, 62 as are known to those skilled in the art. The leg elastic members 60, 62 can be attached to the outer cover 26 and/or the bodyside liner 28 along the opposite longitudinal side edges, 18 and 20, and positioned in the crotch region 16 of the absorbent article 10, 110. The leg elastic members 60, 62 can be parallel to the longitudinal axis 29 as shown in FIGS. 2 and 7 or can be curved as is known in the art. The leg elastic members 60, 62 can provide elasticized leg cuffs.

Additional details regarding each of these elements of the absorbent article 10, 110 described herein can be found below and with reference to the FIGS. 1 through 9.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10, 110. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In some embodiments, the outer cover 26 can be a two layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer of an outer cover 26 can be a 20 gsm spunbond polypropylene non-woven web. The outer layer may also be constructed of the same materials from which the bodyside liner 28 can be constructed as described herein.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent article 10, 110 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent article 10, 110 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent article 10, 110. The absorbent body 34 can have a length and width that can be less than or equal to the length and width of the absorbent article 10, 110.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material.

If a spacer layer is present, the absorbent body 34 can be disposed on the spacer layer and superposed over the outer cover 26. The spacer layer can be bonded to the outer cover 26, for example, by adhesive. In some embodiments, a spacer layer may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer and/or a spacer layer, can be positioned between the absorbent body 34 and the outer cover 26. The absorbent body 34 can be bonded to the fluid transfer layer and/or the spacer layer.

Bodyside Liner:

The bodyside liner 28 of the absorbent article 10, 110 can overlay the absorbent body 34 and the outer cover 26 and can isolate the wearer's skin from liquid waste retained by the absorbent body 34. In various embodiments, a fluid transfer layer can be positioned between the bodyside liner 28 and the absorbent body 34. In various embodiments, an acquisition layer (not shown) can be positioned between the bodyside liner 28 and the absorbent body 34 or a fluid transfer layer, if present. In various embodiments, the bodyside liner 28 can be bonded to the acquisition layer, or to the fluid transfer layer if no acquisition layer is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer, if present, and/or an acquisition layer, if present, and/or a spacer layer, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. The bodyside liner 28 may be narrower than the outer cover 26. However, in other embodiments, the bodyside liner 28 and the outer cover 26 may be of the same dimensions in width and length. In other embodiments, the bodyside liner 28 can be of greater width than the outer cover 26. It is also contemplated that the bodyside liner 28 may not extend beyond the absorbent body 34 and/or may not be secured to the outer cover 26. In some embodiments, the bodyside liner 28 can wrap at least a portion of the absorbent body 34, including wrapping around both longitudinal edges 36, 38 of the absorbent body 34, and/or one or more of the end edges 40, 42. It is further contemplated that the bodyside liner 28 may be composed of more than one segment of material. The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spun-lace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Patent Application Publication No. 2014/0121623 invented by Kirby, Scott S. C. et al.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10, 110. In other aspects, the bodyside liner 28 can be stretchable, and more suitably elastic, in both the lateral and the longitudinal directions 32, 30, respectively.

Containment Flaps:

In an embodiment, the absorbent article 10, 110 can include a pair of containment flaps 50, 52. The containment flaps 50, 52 can be formed separately from the absorbent chassis 11 and attached to the chassis 11 or can be formed integral to the chassis 11. In some embodiments, the containment flaps 50, 52 can be secured to the chassis 11 of the absorbent article 10, 110 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent article 10, 110, through the crotch region 16 to the rear waist region 14 of the absorbent article 10. In some embodiments, the containment flaps 50, 52 can extend in a direction substantially parallel to the longitudinal axis 29 of the absorbent article 10, 110, however, in other embodiments, the containment flaps 50, 52 can be curved, as is known in the art. In other embodiments, such as the absorbent article 110 in FIGS. 6 and 7, the containment flaps 50, 52 can be disposed on the absorbent panel 17 in the crotch region 16.

In embodiments where the containment flaps 50, 52 are coupled to the chassis 11, the containment flaps 50, 52 can be bonded to the bodyside liner 28, the outer cover 26, or another layer, such as a spacer layer, if present, with a barrier adhesive, as is known in the art. Of course, the containment flaps 50, 52 can be bonded to other components of the chassis 11 and can be bonded with other suitable means other than a barrier adhesive. For example, the containment flaps 50, 52 can be bonded to the bodyside liner 28, the outer cover 26, or another layer with pressure bonding, thermal bonding, or ultrasonic bonding. The containment flaps 50, 52 can be constructed of a fibrous material which can be similar to the material forming the bodyside liner 28. Other conventional materials, such as polymer films, can also be employed.

As illustrated in FIGS. 2 and 7, the containment flaps 50, 52 can each include a base portion 64 and a projection portion 66. The base portion 64 can be bonded to the chassis 11, for example, to the bodyside liner 28 or the outer cover 26 as mentioned above. The base portion 64 can include a proximal end 64a and a distal end 64b. The projection portion 66 can be separated from the base portion 64 at the proximal end 64a of the base portion 64. As used in this context, the projection portion 66 is separated from the base portion 64 at the proximal end 64a of the base portion 64 in that the proximal end 64a of the base portion 64 defines a transition between the projection portion 66 and the base portion 64. The proximal end 64a of the base portion 64 can be located where the respective containment flap 50, 52 is bonded to the chassis 11 at the most laterally inward location. For example, if a barrier adhesive bonds the base portion 64 to the bodyside liner 28, then the proximal end 64a of the base portion 64 of each containment flap 50, 52 can be located adjacent the barrier adhesive. In some embodiments, the distal ends 64b of the base portion 64 can laterally extend to the respective longitudinal side edges 18, 20 of the absorbent article 10, 110. In other embodiments, the distal ends 64b of the base portion 64 can end laterally inward of the respective longitudinal side edges 18, 20 of the absorbent article 10, 110. The containment flaps 50, 52 can also each include a projection portion 66 that is configured to extend away from the body facing surface 19 of the chassis 11 at least in the crotch region 16 when the absorbent article 10, 110 is in a relaxed configuration, as illustrated in FIGS. 5A-5F. As shown in FIGS. 2 and 7, the containment flaps 50, 52 can include a tack-down region 71 in either or both of the front waist region 12 and the rear waist region 14 where the projection portion 66 is coupled to the body facing surface 19 of the chassis 11.

It is contemplated that the containment flaps 50, 52 can be of various configurations and shapes, and can be constructed by various methods. For example, the containment flaps 50, 52 of FIGS. 2-5F and 7 depict a vertical containment flap 50, 52 with a tack-down region 71 in both the front and rear waist regions 12, 14 where the projection portion 66 of each containment flap 50, 52 is tacked down to the bodyside liner 28 towards the longitudinal axis 29 of the absorbent article 10. However, it is contemplated that the containment flaps 50, 52 can include a tack-down region 71 where the projection portion 66 of each of the containment flaps 50, 52 is folded back upon itself and coupled to itself and the bodyside liner 28 in a "C-shape" configuration, as is known in the art and described in U.S. Pat. No. 5,895,382 to Robert L. Popp et al. As yet another alternative, it is contemplated that the containment flaps 50, 52 could be constructed in a "T-shape" configuration, such as described in U.S. patent application Ser. No. 13/900,134 by Robert L. Popp et al., which published as U.S. Patent Application Publication 2014/0350504. Such a configuration can also include a tack-down region 71 in either or both of the front and rear waist regions 12, 14, respectively. Of course, other configurations of containment flaps 50, 52 can be used in the absorbent article 10, 110 and still remain within the scope of this disclosure.

The containment flaps 50, 52 can include one or more flap elastic members 68, such as the two flap elastic strands depicted in FIG. 2 (omitted in FIG. 7 for purposes of clarity). Suitable elastic materials for the flap elastic members 68 can include sheets, strands or ribbons of natural rubber, synthetic rubber, or thermoplastic elastomeric materials. Of course, while two elastic members 68 are shown in each containment flap 50, 52, it is contemplated that the containment flaps 50, 52 can be configured with one or three or more elastic members 68. Alternatively or additionally, the containment flaps 50, 52 can be composed of a material exhibiting elastic properties itself.

The flap elastic members 68, as illustrated in FIG. 2, can have two strands of elastomeric material extending longitudinally in the projection portion 66 of the containment flaps 50, 52, in generally parallel, spaced relation with each other. The flap elastic members 68 can be within the containment flaps 50, 52 while in an elastically contractible condition such that contraction of the strands gathers and shortens the projection portions 66 of the containment flaps 50, 52 in the longitudinal direction 30. As a result, the elastic members 68 can bias the projection portions 66 of the containment flaps 50, 52 to extend away from the body facing surface 45 of the absorbent assembly 44 in a generally upright orientation of the containment flaps 50, 52, especially in the crotch region 16 of the absorbent article 10, 110, when the absorbent article 10 is in a relaxed configuration. Such an upright orientation of the projection portion 66 of containment flap 50 is illustrated in the cross-sectional views of FIGS. 5A-5F, where the absorbent article 10 is in a relaxed configuration.

During manufacture of the containment flaps 50, 52 at least a portion of the elastic members 68 can be bonded to the containment flaps 50, 52 while the elastic members 68 are elongated. The percent elongation of the elastic members 68 can be, for example, about 110% to about 350%. In one embodiment, the elastic members 68 can be coated with adhesive while elongated to a specified length prior to attaching to the elastic members 68 to the containment flaps 50, 52. In a stretched condition, the length of the elastic members 68 which have adhesive coupled thereto can provide an active flap elastic region 70 in the containment flaps 50, 52, as labeled in FIG. 2 (omitted in FIG. 7 for purposes of clarity), which will gather upon relaxation of the absorbent article 10, 110. The active flap elastic region 70 of containment flaps 50, 52 can be of a longitudinal length that is less than the length of the absorbent article 10, 110. In this exemplary method of bonding the elastic members 68 to the containment flaps 50, 52, the portion of the elastic members 68 not coated with adhesive, will retract after the elastic members 68 and the absorbent article 10 are cut in manufacturing to form an individual absorbent article 10, 110. As noted above, the relaxing of the elastic members 68 in the active flap elastic region 70 when the absorbent article 10, 110 is in a relaxed condition can cause each containment flap 50, 52 to gather and cause the projection portion 66 of each containment flap 50, 52 to extend away from the body facing surface 19 of the chassis 11 (e.g., the body facing surface 45 of the absorbent assembly 44 or the body facing surface 56 of the bodyside liner 28), as depicted in FIGS. 5A-5F.

Of course, the elastic members 68 can be bonded to the containment flaps 50, 52 in various other ways as known by those of skill in the art to provide an active flap elastic region 70, which is within the scope of this disclosure. Additionally, the active flap elastic regions 70 can be shorter or longer than depicted herein, including extending to the front waist edge 22 and the rear waist edge 24, and still be within the scope of this disclosure.

Leg Elastics:

Leg elastic members 60, 62 can be secured to the outer cover 26, such as by being bonded thereto by laminate adhesive, generally laterally inward of the longitudinal side edges, 18 and 20, of the absorbent article 10, 110. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, for example, between the base portion 64 of each containment flap 50, 52 and the bodyside liner 28, between the base portion 64 of each containment flap 50, 52 and the outer cover 26, or between the bodyside liner 28 and the outer cover 26. The leg elastic members 60, 62 can be one or more elastic components near each longitudinal side edge 18, 20. For example, the leg elastic members 60, 62 as illustrated herein in FIGS. 2 and 7 each include two elastic strands. A wide variety of elastic materials may be used for the leg elastic members 60, 62. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can be omitted from the absorbent article 10, 110 without departing from the scope of this disclosure.

Waist Containment Member:

In an embodiment, the absorbent article 10, 110 can have one or more waist containment members 54, 154, 254, 354, 454, 554. FIGS. 1-5A illustrate a preferred embodiment of a waist containment member 54 on an absorbent article 10, such as a diaper, and FIGS. 6 and 7 illustrate a preferred embodiment of a waist containment member 54 on an absorbent article 110, such as a pant. FIGS. 5B-5F illustrate cross-sectional views of alternative embodiments of a waist containment member 154, 254, 354, 454, 554, respectively, that can be employed as an alternative to or in addition to the waist containment members 54 depicted on the absorbent articles 10, 110 of FIGS. 2 and 7. Because many of the features of the waist containment members 54, 154, 254, 354, 454, and 554 are similar, the discussion below addressing waist containment member 54 of FIGS. 1-5A applies to the alternative waist containment members 154, 254, 354, 454, unless otherwise noted. The unique features to waist containment members 154, 254, 354, 454, and 554 will be discussed in their own right with respect to FIGS. 5B-5F, respectively.

The waist containment member 54 can be disposed in the rear waist region 14. As will be discussed in more detail below, the waist containment member 54 can help contain and/or absorb body exudates, especially low viscosity fecal matter, and as such, can be preferred to be in the rear waist region 14. In some embodiments, the absorbent article 10, 110 can have a waist containment member 54 disposed in the front waist region 12. A waist containment member 54 in the front waist region 12 can help contain and/or absorb body exudates, such as urine, in the front waist region 12. Although not as prevalent as in the rear waist region 14, in some circumstances, fecal material may also spread to the front waist region 12, and thus, a waist containment member 54 disposed in the front waist region 12 can help contain and/or absorb body exudates as well. In other embodiments, the absorbent article 10, 110 can have a waist containment member 54 in both the rear waist region 14 and the front waist region 12.

The waist containment member 54 can be disposed on the body facing surface 45 of the absorbent assembly 44. In some embodiments, such as in embodiments illustrated in FIGS. 1-5F, the waist containment member 54 can be disposed on the body facing surface 56 of the bodyside liner 28. However, in some embodiments, such as the absorbent article 110 in FIG. 7, the waist containment member 54 can be disposed on a body facing surface 58 of the rear waist panel 15.

The waist containment member 54 can include a first longitudinal side edge 72 and a second longitudinal side edge 74. The first longitudinal side edge 72 can be opposite from the second longitudinal side edge 74. The distance between the first longitudinal side edge 72 and the second longitudinal side edge 74 can define a width 51 of the waist containment member 54 in the lateral direction 32, as shown in FIG. 2. Although not depicted, in some embodiments, the first longitudinal side edge 72 can substantially align with the first longitudinal side edge 18 of the absorbent article 10, 110. Similarly, in some embodiments, the second longitudinal side edge 74 can align with the second longitudinal side edge 20 of the absorbent article 10, 110. As illustrated in FIGS. 2 and 7, the waist containment member 54 can be configured such that the first longitudinal side edge 72 can be disposed laterally outward of the proximal end 64a of the base portion 64 of the containment flap 50. Similarly, the waist containment member 54 can be configured such that the second longitudinal side edge 74 can be disposed laterally outward of the proximal end 64a of the base portion 64 of the containment flap 52. The waist containment member 54 can also include an upper lateral edge 75 and a lower lateral edge 88. The first longitudinal side edge 72, the second longitudinal side edge 74, the upper lateral edge 75, and the lower lateral edge 88 are defined when the absorbent article 10, 110 is in the stretched, laid-flat configuration, such as illustrated in FIGS. 2 and 7.

In some embodiments, the width 51 of the waist containment member 54 in the lateral direction 32 as compared to the width 53 of the chassis 11 (as labeled in FIG. 2) can have a ratio of about 0.85 to about 1.00. In some embodiments, the width 51 of the waist containment member 54 in the lateral direction 32 as compared to the width 53 of the chassis 11 can have a ratio of about 0.87 to about 1.00. And in other embodiments, the width 51 of the waist containment member 54 in the lateral direction 32 as compared to the width 53 of the chassis 11 can have a ratio of about 0.90 to about 1.00. For purposes herein, the width 53 of the chassis 11 for use in this ratio is the width of the chassis 11 in the waist region in which the waist containment member 54 is disposed and both width measurements are taken in a direction parallel to the lateral direction 32. Thus, for the examples illustrated herein, the width 51 of the waist containment member 54 can be compared to the width 53 of the chassis 11 in the rear waist region 14. Additionally, the width 51 of the waist containment member 54 in the lateral direction 32 and the width 53 of the chassis 11 as discussed for the ratios herein are to be measured when the absorbent article 10, 110 is in the stretched, laid flat configuration.

As best illustrated in FIGS. 4-5F, the waist containment member 54 can also include a proximal portion 76 and a distal portion 78. The waist containment member 54 can also include an intermediate portion 77. The proximal portion 76 can be coupled to the body facing surface 19 of chassis 11 (e.g., the body facing surface 45 of the absorbent assembly 44 or the body facing surface 56 of the bodyside liner 28). The intermediate portion 77 can be disposed between the proximal portion 76 and the distal portion 78. The intermediate portion 77 can be free to move independent of the proximal portion 76 and the distal portion 78 and can be free to move independent of the body facing surface 19 of the chassis 11 to provide a containment pocket 82 for containing body exudates. In some embodiments, the distal portion 78 can be disposed underneath the intermediate portion 77 when the absorbent article 10 is disposed in the stretched, laid-flat configuration (such as shown in the cross-sectional view in FIG. 4).

Figure 5E:
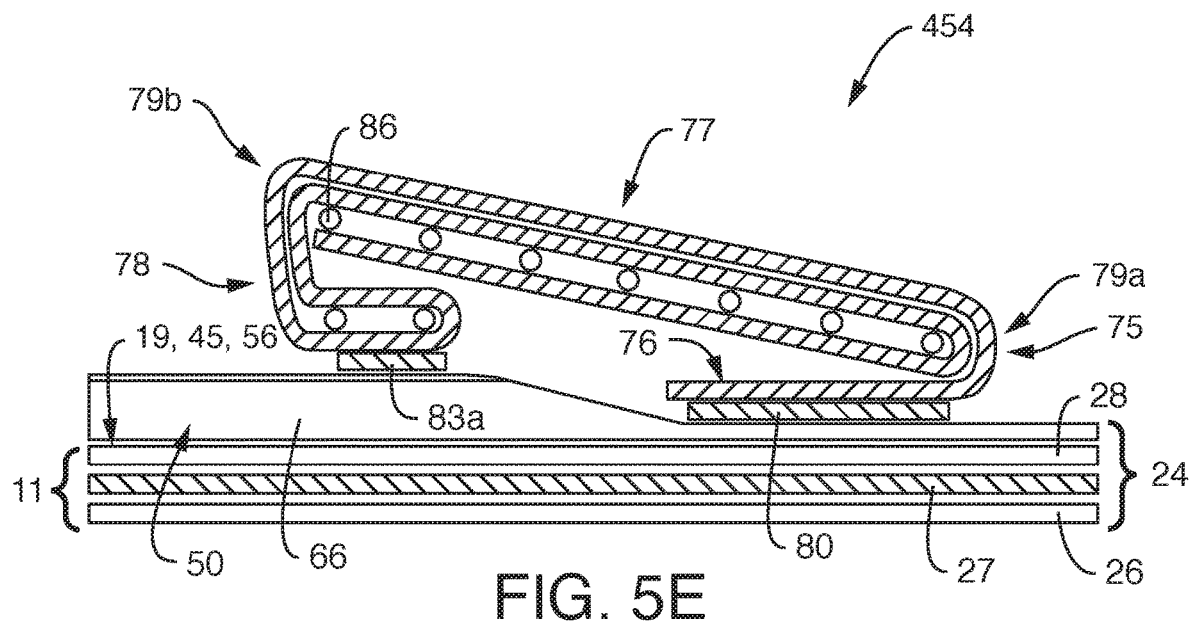
FIG. 5E is a cross-sectional view similar to FIG. 5A, but of an alternative embodiment of a waist containment member.
Figure 5F:
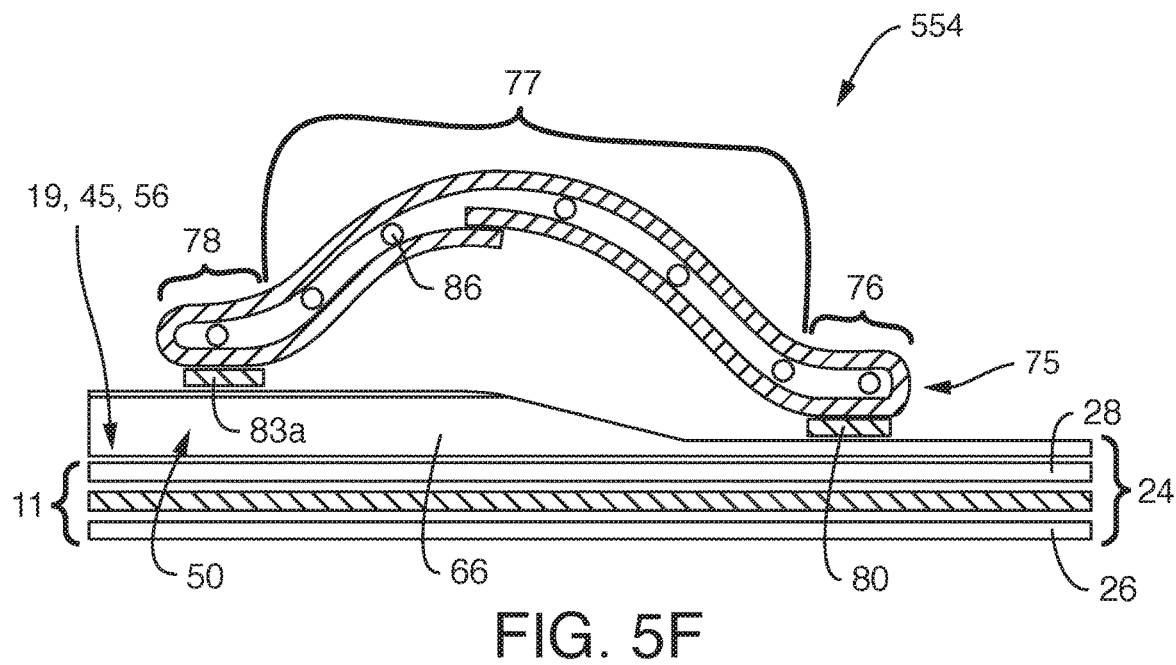
FIG. 5F is a cross-sectional view similar to FIG. 5A, but of an alternative embodiment of a waist containment member.

As illustrated in FIGS. 4-5E, a fold 79a can separate the proximal portion 76 from the intermediate portion 77. As used in this context, the fold 79a separates the proximal portion 76 from the intermediate portion 77 in that the fold 79a defines a transition between the proximal portion 76 and the intermediate portion 77. The fold 79a can define the upper lateral edge 75 of the waist containment member 54 when the absorbent article 10, 110 is in the stretched, laid-flat configuration. A fold 79b can separate the intermediate portion 77 from the distal portion 78. As used in this context, the fold 79b separates the intermediate portion 77 from the distal portion 78 in that the fold 79b defines a transition between the intermediate portion 77 and the distal portion 78. The fold 79b can define the lower lateral edge 88 of the waist containment member 54 when the absorbent article 10, 110 is in the stretched, laid-flat configuration. Folds 79a and 79b can be created in the method 610 of manufacturing the absorbent article 10, 110 including the waist containment member 54, as will be discussed in further detail below.

The proximal portion 76 can be coupled to the body facing surface 19 of the chassis 11 with an adhesive 80, and in some embodiments, the proximal portion 76 can be coupled to the body facing surface 45 of the absorbent assembly 44. In some embodiments, such as in embodiments illustrated in FIGS. 2-5F, the proximal portion 76 of the waist containment member 54 can be coupled to the body facing surface 56 of the bodyside liner 28. However, in some embodiments, such as the absorbent article 110 in FIG. 7, the proximal portion 76 of the waist containment member 54 can be coupled to the body facing surface 58 of the rear waist panel 15. The proximal portion 76 can be coupled to the body facing surface 45 of the absorbent assembly 44 with adhesive 80 along the entire length of the proximal portion 76 in the longitudinal direction 30, however, it is contemplated that only a portion of the proximal portion 76 in the longitudinal direction 30 can be coupled to the body facing surface 45 of the absorbent assembly 44. Of course, it is contemplated that the proximal portion 76 of the waist containment member 54 can be coupled to the body facing surface 19 of the chassis 11 or the body facing surface 45 of the absorbent assembly 44 by means other than an adhesive 80, such as by pressure bonding, ultrasonic bonding, thermal bonding, and combinations thereof. In preferred embodiments, the proximal portion 76 is coupled to the body facing surface 19 of the chassis 11 in the lateral direction 32 in a constant fashion, as opposed to an intermittent fashion, such that a longitudinal barrier to body exudates is formed between the proximal portion 76 and the body facing surface 19 of the chassis 11.

In some embodiments, the proximal portion 76 of the waist containment member 54 can include a longitudinal length measured in the longitudinal direction 30 that is shorter than a longitudinal length of the distal portion 78 of the waist containment member 54. As illustrated in the embodiment depicted in FIGS. 4-5F, the proximal portion 76 of the waist containment member 54 can include a longitudinal length measured in the longitudinal direction 30 that is shorter than a longitudinal length of the intermediate portion 77 and the longitudinal length of the distal portion 78 of the waist containment member 54 combined. However in some embodiments, the longitudinal length of the proximal portion 76 can be substantially equal to or larger than the longitudinal length of the intermediate portion 77 and the longitudinal length of the distal portion 78 of the waist containment member 54. For purposes herein, the longitudinal length of the proximal portion 76, the longitudinal length of the intermediate portion 77, and the longitudinal length of the distal portion 78 of the waist containment member 54 are measured when the absorbent article 10, 110 is in the stretched, laid flat configuration.

Figure 3:
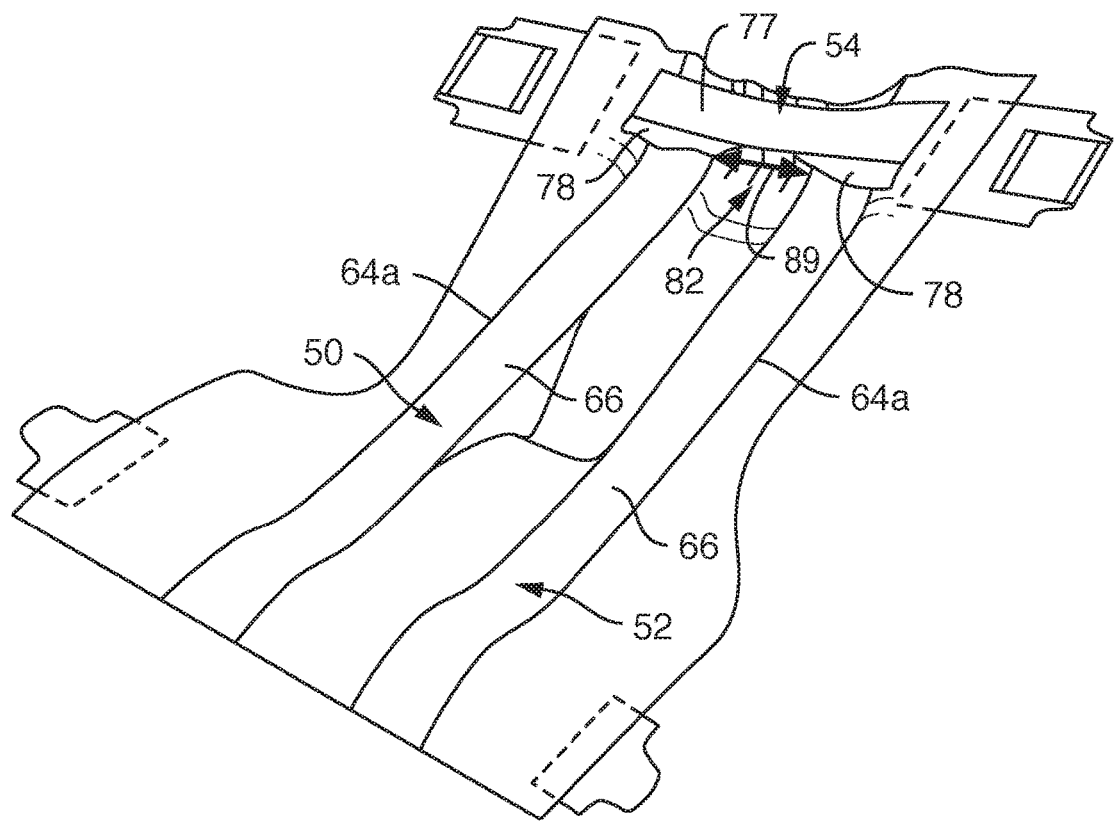
FIG. 3 is a top perspective view of the absorbent article of FIG. 2 in an unfastened, relaxed condition.

As illustrated in FIG. 3, because the intermediate portion 77 of the waist containment member 54 can freely move independent of the proximal portion 76 and the body facing surface 19 of the chassis 11 when the absorbent article 10, 110 is in the relaxed configuration, the intermediate portion 77 can help provide a containment pocket 82 when the absorbent article 10, 110 is in the relaxed configuration. The containment pocket 82 can help provide a barrier to contain and/or can help absorb body exudates. The containment pocket 82 can be especially beneficial for containing and/or absorbing low viscosity fecal matter, which can be prevalent in younger children. As previously noted, the first longitudinal side edge 72 can be disposed laterally outward of the proximal end 64a of the base portion 64 of the containment flap 50, and thus, the containment pocket 82 can extend laterally outward of the proximal end 64a of the containment flap 50. Similarly, the second longitudinal side edge 74 can be disposed laterally outward of the proximal end 64a of the base portion 64 of the containment flap 52 and the containment pocket 82 can extend laterally outward of the proximal end 64a of the containment flap 52. Such a configuration provides waist containment member 54 with a wide containment pocket 82 to contain and/or absorb body exudates.

Once exudates enter the containment pocket 82 provided by the waist containment member 54, the waist containment member 54 can be configured to help retain the body exudates within the pocket 82. For example, in some embodiments, the waist containment member 54 can include a first longitudinal tack-down region 84a and a second longitudinal tack-down region 84b. The waist containment member 54 can additionally or alternatively include a first lateral tack-down region 83a and a second lateral tack-down region 83b, as illustrated in FIGS. 2 and 7.

The first and second longitudinal tack-down regions 84a, 84b can help prevent lateral flow of body exudates that enter the containment pocket 82 of the waist containment member 54. The longitudinal tack-down regions 84a, 84b can be formed by coupling the intermediate portion 77 to the proximal portion 76 of the waist containment member 54 and/or the body facing surface 19 of the chassis 11 and/or the distal portion 78 of the waist containment member 54 and by coupling the distal portion 78 of the waist containment member to the body facing surface 19 of the chassis 11 near the first and second longitudinal side edges 72, 74, respectively, of the waist containment member 54. For example, FIGS. 2, 4, and 7 illustrate several short, transverse lines of adhesive 81a, 81b along the longitudinal side edges 72, 74 that can help provide for the longitudinal tack-down regions 84a, 84b. As best illustrated in the cross-sectional view of FIG. 4, the adhesive 81b can couple the distal portion 78 to the body facing surface 19 of the chassis 11. The adhesive 81a can couple the intermediate portion 77 of the waist containment member 54 to the distal portion 78 of the waist containment member 54 and/or to the body facing surface 19 of the chassis 11 and/or to the proximal portion 76 of the waist containment member 54. Although the lines of adhesive 81a are shown as intermittent in the longitudinal direction 30 near each of the longitudinal side edges 72, 74 in that the adhesive 81a does not extend continuously from the lower lateral edge 88 to the upper lateral edge 75 of the waist containment member 54, it is contemplated that the adhesive 81a could be in a continuous fashion in the longitudinal direction 30. Additionally, it is contemplated that the longitudinal tack-down regions 84a, 84b could be provided by other means of bonding other than adhesives 81a, 81b, including pressure bonding, thermal bonding, ultrasonic bonding, and combinations thereof.

The first lateral tack-down region 83a and the second lateral tack-down region 83b can help prevent the longitudinal flow of body exudates that that enter the containment pocket 82 of the waist containment member 54. The first lateral tack-down region 83a and the second lateral tack-down region 83b can also help form part of the first and second longitudinal tack-down regions 84a, 84b, respectively. The first lateral tack-down region 83a can include the distal portion 78 of the waist containment member 54 being coupled to the body facing surface 19 of the chassis 11 from the first longitudinal side edge 72 towards the lateral axis 29 of the absorbent article 10, 110. In preferred embodiments that include containment flaps 50, 52, the first lateral tack-down region 83a can include the distal portion 78 of the waist containment member 54 being coupled to the body facing surface 19 of the chassis 11 from the first longitudinal side edge 72 towards the proximal end 64a of the base portion 64 of the containment flap 50. The second lateral tack-down region 83b can include the distal portion 78 of the waist containment member 54 being coupled to the body facing surface 19 of the chassis 11 from the second longitudinal side edge 74 towards the lateral axis 29 of the absorbent article 10, 110. In preferred embodiments that include containment flaps 50, 52, the second lateral tack-down region 83b can include the distal portion 78 of the waist containment member 54 being coupled to the body facing surface 19 of the chassis 11 from the second longitudinal side edge 74 towards the proximal end 64a of the base portion 64 of the containment flap 52.

In some embodiments, the first and second lateral tack-down regions 83a, 83b can be configured such that the distal portion 78 of the waist containment member 54 can be coupled to the respective containment flaps 50, 52. In some embodiments, the first lateral tack-down region 83a laterally extends to at least the proximal end 64a of the base portion 64 of the containment flap 50, and more preferably, to the projection portion 66 of the containment flap 50 (as illustrated in FIGS. 2 and 7). In some embodiments, the second lateral tack-down region 83b laterally extends to at least the proximal end 64a of the base portion 64 of the containment flap 52, and more preferably, to the projection portion 66 of the containment flap 52 (as illustrated in FIGS. 2 and 7). Thus, the distal portion 78 of the waist containment member 54 can be coupled to the base portion 64 of each containment flap 50, 52.

The first and second lateral tack-down regions 83a, 83b can couple the distal portion 78 of the waist containment member 54 to the body facing surface 19 of the chassis 11 with an adhesive as shown in FIGS. 2, 4, 5A-5F, and 7. However, it is contemplated that other method of coupling could be used to form the first and second lateral tack-down regions 83a, 83b, including pressure bonding, thermal bonding, ultrasonic bonding, and combinations thereof.

As illustrated in FIGS. 2 and 7, the first and second lateral tack-down regions 83a, 83b do not extend across the entire width 51 of the waist containment member 54. Instead, a gap 89 is provided in the lateral direction 32 between the first and second lateral tack-down regions 83a, 83b. As illustrated in FIG. 3, the gap 89 can provide an entrance for body exudates to enter the containment pocket 82 created by the waist containment member 54. In some embodiments, the gap 89 between the first and second lateral tack-down regions 83a, 83b can be equal to the distance between the projection portions 66 of the containment flaps 50, 52.

As illustrated in FIGS. 2, 4, and 7, the first lateral tack-down region 83a can be located away from the lower lateral edge 88 of the waist containment member 54 when the absorbent article 10, 110 is in the stretched, laid-flat configuration. Similarly, the second lateral tack-down region 83b can be located away from the lower lateral edge 88 of the waist containment member 54 when the absorbent article 10, 110 is in the stretched, laid-flat configuration. In other words, the first and second lateral tack-down regions 83a, 83b do not extend to the lower lateral edge 88 when the absorbent article 10, 110 is in the stretched, laid-flat configuration. In a preferred embodiment, the first lateral tack-down region 83a and the second lateral tack-down region 83b are disposed at least about 3.0 mm away from the lower lateral edge 88 of the waist containment member 54 when the absorbent article 10, 110 is in the stretched, laid-flat configuration. In other embodiments, the first and second lateral tack-down regions 83a, 83b can be located at least about 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, or 30.0 mm or more away from the lower lateral edge 88 of the waist containment member 54 when the absorbent article 10, 110 is in the stretched, laid-flat configuration. Of course, it is contemplated that the first and second lateral tack-down regions 83a, 83b can be located a further distance away from the lower lateral edge 88 of the waist containment member 54 than this exemplary range. By configuring the first and second lateral tack-down regions 83a, 83b to be disposed away from the lower lateral edge 88 of the waist containment member 54, the waist containment member 54 is able to provide more void volume near the longitudinal sides 72, 74 of the waist containment member 54 when the absorbent article 10, 110 is in the relaxed configuration as illustrated in FIGS. 3 and 5A-5E.

For example, as illustrated in FIG. 5A, by locating the distal portion 78 of the waist containment member 54 underneath the intermediate portion 77 and disposing the first and second lateral tack-down regions 83a, 83b away from the lower lateral edge 88 of the waist containment member 54, some of the distal portion 78 as well as the intermediate portion 77 can extend away from the body-facing surface 19 of the chassis 11 (e.g., the body-facing surface 56 of the bodyside liner 28), when the absorbent article 10 is in the relaxed configuration, such as when the absorbent article 10 is placed on the wearer. In other words, by folding the distal portion 78 underneath the intermediate portion 77 by fold 79b, the waist containment member 54 is gathered in the longitudinal direction 30 such that the waist containment member 54 can extend away from the body facing surface 19 of the chassis 11 to provide a containment pocket 82 for containing exudates between the first lateral tack-down region 83a and the upper lateral edge 75 of the waist containment member 54 and between the second lateral tack-down region and between the upper lateral edge 75 of the waist containment member 54.

Another way to achieve the increased void volume of the containment pocket 82 created by the waist containment member 554 is illustrated in the alternative embodiment of FIG. 5F. The waist containment member 554 of FIG. 5F is comprised of a single layer of material that wraps seven elastic members 86 to form a laminate. Rather than folding the waist containment member 554 to provide a distal portion 78 that is disposed underneath the intermediate portion 77 to gather the waist containment member 554 to provide void volume, the waist containment member 554 in FIG. 5F gathers, or scrunches, the material forming the waist containment member 554 in the longitudinal direction 30 without folding the distal portion 78 of the waist containment member 554 underneath the intermediate portion 77 of the waist containment member 554. As illustrated in FIG. 5F, the waist containment member 554 can still include lateral tack-down regions 83a, 83b (83b not shown), but the lateral tack-down regions 83a, 83b are preferably located at the lower lateral edge 88 of the waist containment member 554, not away from the lower lateral edge 88 of the waist containment member 554 such as described above with respect to the embodiments disclosed in FIGS. 5A-5E. The material forming the waist containment member 554 can be gathered as illustrated in FIG. 5F by mechanical gathering the material before coupling it to the body facing surface 19 of the chassis 11 or by stretching the material forming the waist containment member 554 in the longitudinal direction 30 prior to coupling the waist containment member 554 to the body facing surface 19 of the chassis 11. Either way, the waist containment member 554 can create additional void volume for the containment pocket 82 without disposing the distal portion 78 of the waist containment member 554 underneath the intermediate portion 77, as in other embodiments discussed herein.

As illustrated in FIGS. 5A-5E, the waist containment member 54, 154, 254, 354, 454, including a proximal portion 76, an intermediate portion 77, and a distal portion 78 disposed underneath the intermediate portion 77, can be formed in various configurations. For example, the waist containment members 54, 154, and 454 as illustrated in FIGS. 5A, 5B, and 5E, respectively, can be formed from a single piece of material. Alternatively, the waist containment members 254, 354 as illustrated in FIGS. 5C and 5D, respectively, can be formed from more than one piece of material.

For example, the waist containment member 254 shown in FIG. 5C includes one piece of material forming the distal portion 78, with another piece of material forming the intermediate portion 77 and the proximal portion 76, the material forming the intermediate portion 77 being folded over upon itself to envelope elastic members 86. The two pieces of material of the waist containment member 254 can be joined with an adhesive 87, such as near fold 79b. As illustrated in FIG. 5D, waist containment member 354 includes two different pieces of material that overlap one another to form the intermediate portion 77 and laminate elastic members 86. The two pieces of material in the waist containment member 354 can be joined by adhesive (not shown) covering the elastic members 86 as is known in the art. By having the waist containment member 254, 254 be formed from two different pieces of material, the different pieces of material can be configured to provide different properties according to desired functions. For example, in the embodiments illustrated in FIGS. 5C and 5D, the material forming the proximal portion 76 and the intermediate portion 77 can be selected to have properties of greater softness as compared to the material forming the distal portion 76, since the material forming the proximal portion 76 and the intermediate portion 77 can have more contact with the wearer's skin.

In the embodiments illustrated in FIGS. 5A-5E, the waist containment members 54, 154, 254, 354, 454 all have an intermediate portion 77 that is thicker than the proximal portion 76. Such a configuration provides the benefit of reducing strike-through of body exudates from the containment pocket 82 through the material(s) forming the intermediate portion 77, yet reduces the amount of material(s) at the proximal portion 76 where such thickness is not necessary. For example, the waist containment members 54, 254, and 354 of FIGS. 5A, 5C, and 5D, respectively, have twice the thickness in the intermediate portion 77 as compared to the thickness of the proximal portion 76. The waist containment members 154 and 454 of FIGS. 5B and 5E, respectively, have triple the thickness as compared to the thickness of the proximal portion 76. The additional thickness in the intermediate portion 77 as compared to the proximal portion 76 can also provide the benefit of additional softness of the waist containment member 54, 154, 254, 354, 454 against the wearer's skin. Yet another benefit of additional thickness in the intermediate portion 77 is increased opacity towards the containment pocket 82 formed by the waist containment member 54, 154, 254, 354, 454, which can provide the desirable benefit of masking the presence of body exudates when the absorbent article 10, 110 is being changed by the wearer or a caregiver.

In preferred embodiments, and as illustrated in FIGS. 2, 5A-5F, and 7, the first and second lateral tack-down regions 83a, 83b of the waist containment members 54, 154, 254, 354, 454, 554 can synergistically work with the containment flaps 50, 52 to better guide and contain body exudates within the containment pocket 82. As previously noted, the first and second lateral tack-down regions 83a, 83b preferably extend at least to the proximal end 64a of the base portion 64 of the respective containment flaps 50, 52, and more preferably, extend to the projection portion 66 of the respective containment flaps 50, 52. In doing so, the containment flaps 50, 52 can guide body exudates into the containment pocket 82, and the first and second lateral tack-down regions 83a, 83b can act as longitudinal barriers preventing the body exudates from escaping from the containment pocket 82 if and when the body exudates disperse laterally outside of the projection portions 66 of the containment flaps 50, 52 once within the containment pocket 82.

Additionally or alternatively, the tack-down regions 71 of the containment flaps 50, 52 can be configured to not extend to the lower lateral edge 88 of the waist containment member 54, 154, 254, 354, 454, 554, thus allowing the projection portion 66 of each of the containment flaps 50, 52 to extend away from the body facing surface 19 of the chassis 11 and guide the body exudates longitudinally further into the containment pocket 82. By keeping the tack-down regions 71 away from the lower lateral edge 88 of the waist containment member 54, 154, 254, 354, 454, 554, the active flap elastic region 70 of the containment flaps 50, 52 can extend into the containment pocket 82, and more preferably, can extend to the first and second lateral tack-down regions 83a, 83b, as illustrated in FIGS. 2, 5A, and 7. In such configurations, the active flap elastic region 70 of each containment flap 50, 52 can provide a lifting force on the waist containment member 54, 154, 254, 354, 454, 554 to help the waist containment member 54, 154, 254, 354, 454, 554 extend away from the body facing surface 19 of the chassis 11 to provide more void volume and a more open containment pocket 82 for body exudates to enter, and the first and second lateral tack-down regions 83a, 83b can provide the longitudinal barrier to body exudates once the body exudates have entered the containment pocket 82.

In preferred embodiments, the waist containment member 54 can include at least one elastic member 86. In some embodiments, such as the embodiments depicted in FIG. 5A, the waist containment member 54 can include multiple elastic members 86, such as eight elastic members 86 (only one of the elastic members 86 is labeled in FIG. 5A for purposes of clarity). The waist containment members 154, 254, 354, 454, 554 of FIGS. 5B-5F include multiple elastic members 86 (only one elastic member 86 is labeled for purposes of clarity). Of course, it is contemplated that the waist containment member 54 can include other amounts of elastic members 86 other than eight, and in some embodiments, need not include any elastic members 86. In some embodiments, the elastic members 86 can be spaced evenly in the longitudinal direction 30 of the waist containment member 54. The elastic member 86 can span substantially from the first longitudinal side edge 72 to the second longitudinal side edge 74 of the waist containment member 54. The elastic member 86 can be disposed in the intermediate portion 77 of the waist containment member 54 and be located near the lower lateral edge 88 of the waist containment member 54 when the absorbent article 10, 110 is in the stretched, laid-flat configuration. Additionally or alternatively, the elastic member 86 can be located in a distal portion 78 of the waist containment member 54, 454, 554, such as illustrated in FIGS. 5A, 5E, and 5F.

A wide variety of elastic materials may be used for the elastic member(s) 86 in the waist containment member 54. Suitable elastic materials can include sheets, strands or ribbons of natural rubber, synthetic rubber, elastic foams, or thermoplastic elastomeric materials (e.g., films). The elastic materials can be stretched and secured to a substrate forming the waist containment member 54, secured to a gathered substrate, or secured to a substrate and then elasticized or shrunk, for example, with the application of heat, such that the elastic retractive forces are imparted to the substrate forming the waist containment member 54.

As depicted in FIG. 2, in some embodiments the waist containment member 54 can be disposed on the body facing surface 19 of the chassis 11 such that a gap 85 is provided between the second end edge 42 of the absorbent body 34 and the lower lateral edge 88 of the waist containment member 54. By providing a gap 85, the containment pocket 82 can have a greater void volume for body exudates. Additionally, it is believed that gap 85 can help body exudates enter the containment pocket 82 of the waist containment member 54.

The waist containment member 54 can be comprised of a variety of materials. In a preferred embodiment, the waist containment member 54 can be comprised of a spunbond-meltblown-spunbond ("SMS") material. However it is contemplated that the waist containment member 54 can be comprised of other materials including, but not limited to, a spunbond-film-spunbond ("SFS"), a bonded carded web ("BCW"), or any non-woven material. In some embodiments, the waist containment member 54 can be comprised of a laminate of more than one of these exemplary materials, or other materials. In some embodiments, the waist containment member 54 can be comprised of a liquid impermeable material. In some embodiments, the waist containment member 54 can be comprised of a material coated with a hydrophobic coating. The basis weight of the material forming the waist containment member 54 can vary, however, in a preferred embodiment, the basis weight can be between about 8 gsm to about 120 gsm, not including the elastic members 86 in the waist containment member 54. More preferably, the basis weight of the material comprising the waist containment member 54 can be between about 10 gsm to about 40 gsm, and even more preferably, between about 15 gsm to about 25 gsm.

Fastening System:

In an embodiment, the absorbent article 10 can include a fastening system. The fastening system can include one or more back fasteners 91 and one or more front fasteners 92. The embodiments shown in FIGS. 1, 2, and 5 depict embodiments with one front fastener 92. Portions of the fastening system may be included in the front waist region 12, rear waist region 14, or both.

The fastening system can be configured to secure the absorbent article 10 about the waist of the wearer in a fastened condition as shown in FIG. 1 and help maintain the absorbent article 10 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIG. 2. As shown in FIG. 5B, in some embodiments the waist containment member 54 can extend to back fasteners 91. In some embodiments, the waist containment member 54 can be coupled to the stretch component 94 of the back fasteners 91, either directly or indirectly. In some embodiments, the waist containment member 54 can extend to the longitudinal side edges 18, 20 of the absorbent article 10.

Figure 8:
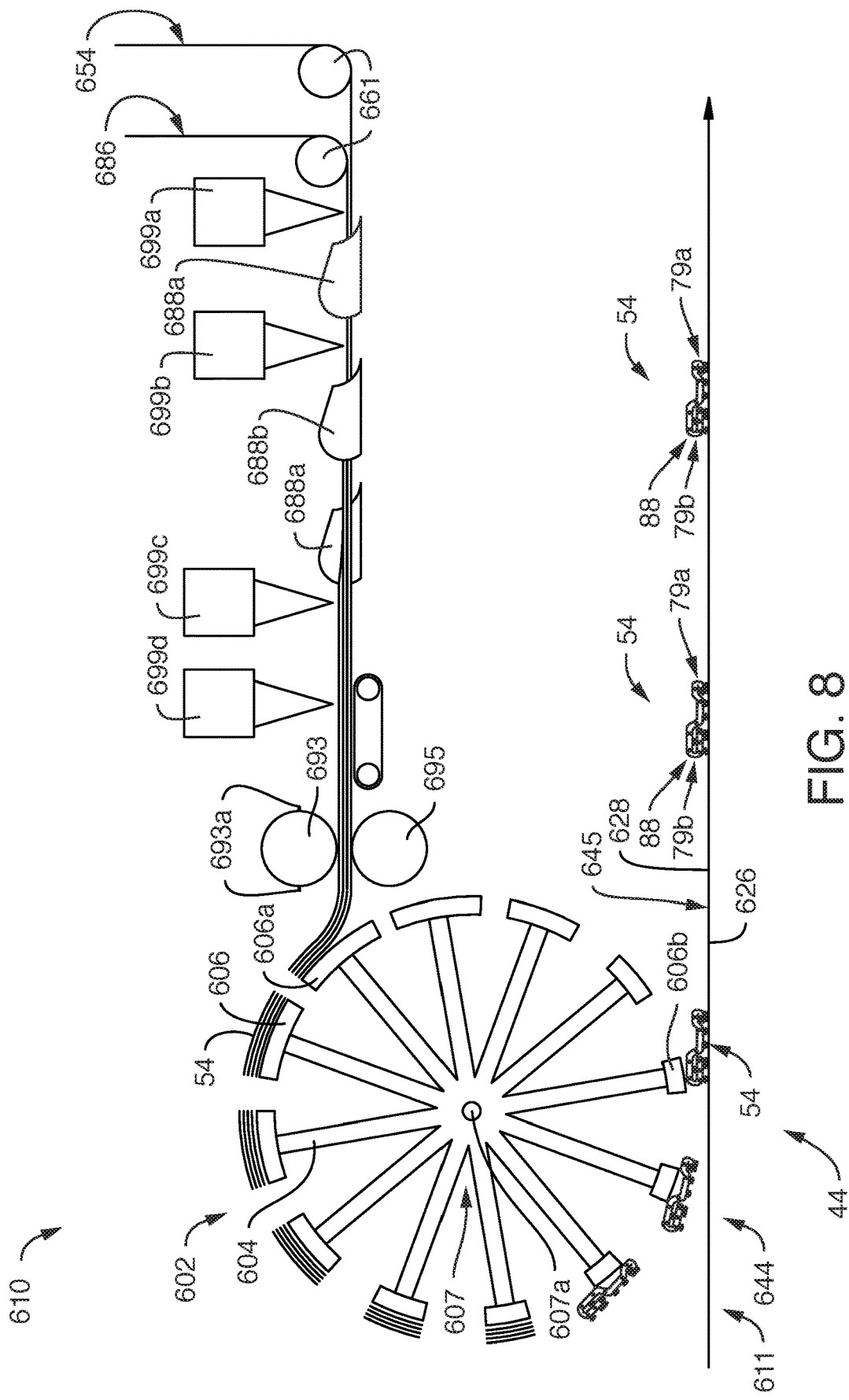
FIG. 8 is a process schematic depicting an exemplary embodiment of a method of manufacturing an absorbent article including a waist containment member.
Figure 9:
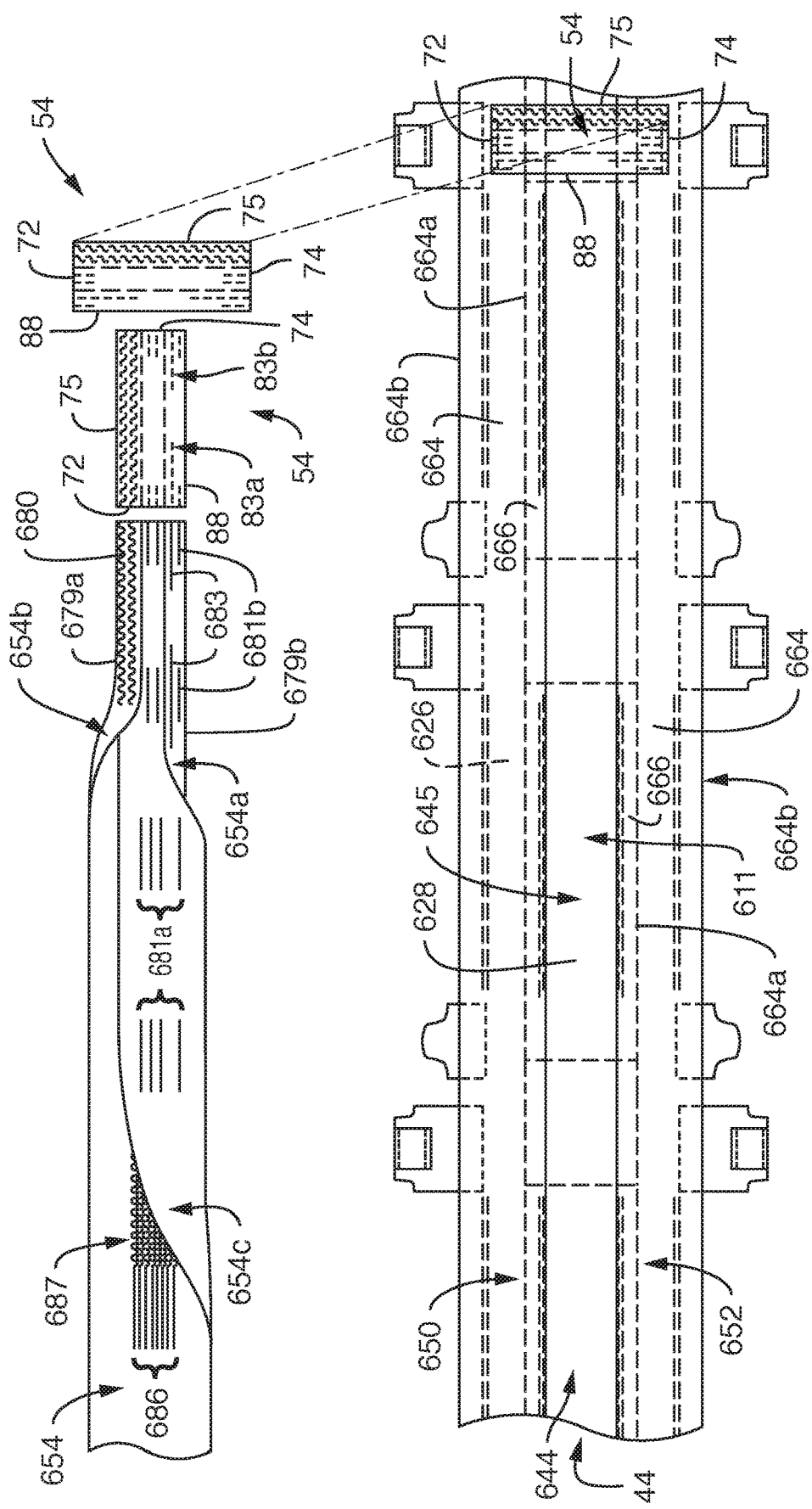
FIG. 9 is a process schematic depicting some of the steps of forming the waist containment member of the method depicted in FIG. 8.

Method of Manufacturing an Absorbent Article:

With reference to FIGS. 8 and 9, an exemplary method 610 of manufacturing an absorbent article 10 with a waist containment member 54 as depicted in FIGS. 1-5A will now be described. The method 610 can include providing a chassis 11, which can be in the form of a chassis web 611. The chassis 11 (e.g., chassis web 611) can include an absorbent assembly 44. The absorbent assembly 44 can be in a discrete form of the chassis 11 for an absorbent article 10 as discussed above, or can be provided in form of an absorbent assembly web 644 as part of a chassis web 611. The absorbent assembly 44 (absorbent assembly web 644) can include a bodyside liner 28 and an outer cover 26, which can be in web form as a bodyside liner web 628 and an outer cover web 626 as well. The absorbent assembly web 644 can include a body facing surface 645.

The method 610 can include providing a pair of containment flaps 650, 652, as are discussed above, and that can each include a base portion 664 and a projection portion 666. The method 610 can also include bonding the base portion 664 of each of the containment flaps 650, 652 to the body facing surface 45 of the absorbent assembly 44 (e.g., the body facing surface 645 of the absorbent assembly web 644). In some embodiments, bonding the base portion 664 of each of the containment flaps 650, 652 to the body facing surface 45 of the absorbent assembly 44 can include bonding the base portion 664 of each of the containment flaps 650, 652 to the bodyside liner 28 (e.g., bodyside liner web 628). In other embodiments, bonding the base portion 664 of each of the containment flaps 650, 652 to the body facing surface 45 of the absorbent assembly 44 can include bonding the base portion 664 of each of the containment flaps 650, 652 to the outer cover 26 (e.g., outer cover web 626). As noted above, the base portion 664 of each of the containment flaps 650, 652 can include a proximal end 664a and a distal end 664b.

The method 610 can also include providing a continuous web of waist containment member material 654. The continuous web of waist containment member material 654 can be guided over one or more idlers 661, as are known in the art. The continuous web of waist containment member material 654 can be folded such that at least a portion 654a of the continuous web of waist containment member material 654 is folded upon itself. Folding the continuous web of waist containment member material 654 can provide a folded edge 679b that, once the continuous web of waist containment member material 654 is cut to form a waist containment member 54, will separate the distal portion 78 of the waist containment member 54 from the intermediate portion 77 of the waist containment member 54 at fold 79b, as discussed above with respect to FIGS. 1-5A. With such a fold, the distal portion 78 can be folded against the intermediate portion 77. Folding the portion 654a of the continuous web of waist containment member material 654 can be accomplished with a folding board 688b, as is known in the art.

In some embodiments, the method 610 can also include folding a portion 654b of the continuous web of waist containment member material 654 upon itself to provide a folded edge 679a, that once the continuous web of waist containment member material 654 is cut to form a waist containment member 54, will separate the intermediate portion 77 of the waist containment member 54 from the proximal portion 76 of the waist containment member 54 at fold 79a, as discussed above with respect to FIGS. 1-5A. With such a fold, the proximal portion 76 can be folded against the intermediate portion 77. Folding the portion 654b of the continuous web of waist containment member material 654 can be accomplished with a folding board 688c, as is known in the art.

In some embodiments, the method 610 can also include folding a portion 654c of the continuous web of waist containment member material 654 upon itself to cover elastic members 686 (as described below) and/or to form a greater thickness in the intermediate portion 77 of the waist containment member 54, which is formed once the continuous web of waist containment member material 654 is cut. Folding the portion 654c of the continuous web of waist containment member material 654 can be accomplished with a folding board 688a, as is known in the art. As illustrated in FIGS. 8 and 9, in this preferred embodiment, portion 654c can be folded first by folding board 688a, then portion 654a can be folded by folding board 688b, then portion 654b can be folded by folding board 688c.

In some embodiments, the method 610 can further include providing an elastic member 86, which can be in the form of an elastic member web 686. In some embodiments, more than one elastic member 86 can be provided. For example, in some embodiments, eight elastic member webs 686 can be provided. The elastic member web(s) 686 can be bonded to the continuous web of waist containment member material 654. In one embodiment, an adhesive station 699a can apply an adhesive 687 (as shown in FIG. 9) to the elastic member web(s) 686 to bond the elastic member web(s) 686 to the continuous web of waist containment member material 654. The adhesive 687 can be applied in a spray fashion, or in any other suitable fashion. In some embodiments, the adhesive 687 could be applied to the continuous web of waist containment member material 654 in addition to or in the place of applying the adhesive 687 to the elastic member web(s) 686. Folding a portion 654c of the continuous web of waist containment member material 654 upon itself with folding board 688a can provide for wrapping the elastic member web(s) 686, as discussed above.

The method 610 can also include providing an intermittent adhesive 681a to the continuous web of waist containment member material 654. In one embodiment, the intermittent adhesive 681a can be applied intermittently to the continuous web of waist containment member material 654 by pulsing multiple lines of adhesive 681a with an adhesive station 699b. As previously mentioned, it is contemplated that the intermittent adhesive 681a could be applied as a singular continuous adhesive across the width of the continuous web of waist containment member material 654, rather than in discrete segments as shown in FIG. 9.

The method 610 can also include providing an intermittent adhesive 681b to the continuous web of waist containment member material 654. The intermittent adhesive 681b can be applied to the folded portion 654a near folded edge 679b and can be applied by adhesive station 699c. Along with intermittent adhesive 681a, the intermittent adhesive 681b can help form the longitudinal tack-down regions 84a, 84b, as previously discussed with respect to FIGS. 2, 4, and 7, once the continuous web of waist containment member material 654 is cut to form a web containment member 54.

The method 610 can also include applying intermittent adhesive 683 to the continuous web of waist containment member material 654. The intermittent adhesive 683 can also be applied by adhesive station 699c, or can be applied by its own adhesive station. Importantly, the adhesive 683 can be applied away from the folded edge 679b of the continuous web of the waist containment member material 654, which once the continuous web of waist containment member material 654 is cut and applied to the chassis 11 to form a waist containment member 54, the adhesive 683 will form the lateral tack-down regions 83a, 83b of the waist containment member 54. In other words, the adhesive 683 does not extend to the folded edge 679b of the continuous web of the waist containment member material 654. It can also be seen that the intermittent adhesive 683 can be applied for a longer length than the intermittent adhesives 681a, 681b. Because the intermittent adhesive 683 can be applied to the continuous web of waist containment member material 654 such that once the continuous web of waist containment member material 654 is cut the intermittent adhesive 683 will be near the longitudinal side edges 72, 74 of the waist containment member 54, the adhesive 683 can also help form the longitudinal tack-down regions 84a, 84b along with the intermittent adhesives 681a, 681b discussed above.

It is contemplated that one or more of the adhesives 681a, 681b, and 683 could be substituted for other bonding methods to bond the respective portions of the waist containment member 54 to the chassis 11. For example, it is contemplated that the intermittent adhesive 681a and 681b could be substituted with a bonding unit that would intermittently bond the continuous web of waist containment member material 654 to itself and to the chassis 11 to form the longitudinal tack-down regions 84a, 84b discussed above. Furthermore, it is also contemplated that the lateral tack-down regions 83a, 83b could be formed by bonding the waist containment member 54 to the chassis 11 as described above via pressure bonding, thermal bonding, ultrasonic bonding, other combinations thereof, after the continuous web of waist containment member material 654 is cut to form the waist containment member 54 and is applied to the chassis 11.

In some embodiments, the method 610 can further include applying an adhesive 680 to the continuous web of waist containment member material 654. Adhesive 680 can be applied via adhesive station 699d and can be applied to the portion 654b of the continuous web of the waist containment member material 654 that is folded, and that once cut, will form the proximal portion 76 of the waist containment member 54. The adhesive 680 can bond the waist containment member 54 to the chassis 11 of the absorbent article 10 (e.g., the chassis web 611), as discussed further below.

The method 610 can additionally include cutting the continuous web of waist containment member material 654 into a discrete waist containment member 54. As illustrated in FIG. 8, the continuous web of waist containment member material 654 can be cut by a knife roll 693 including one or more knives 693a (two are shown in FIG. 8) and an anvil roll 695, as is known in the art. The anvil roll 695 can supply a vacuum pressure (i.e., a negative pressure) through one or more holes in the outer surface of the anvil roll 695 to help secure the continuous web of waist containment member material 654 to the anvil roll 695. The continuous web of waist containment member material 654 can be delivered to the anvil roll 695 at any suitable rate. As depicted in FIG. 9, the continuous web of waist containment member material 654 can be cut near the middle of where the intermittent adhesives 681a, 681b and intermittent adhesive 683 are applied to provide the longitudinal tack-down regions 84a, 84b and the lateral tack-down regions 83a, 83b for the waist containment member 54 near the first longitudinal side edge 72 and the second longitudinal side edge 74 in adjacent waist containment members 54.

The knife roll 693 and anvil roll 695 can cut the continuous web of waist containment member material 654 completely when each knife 693a comes into contact with the anvil roll 695. Alternatively, the knife roll 693 and the anvil roll 695 can be configured to perforate the continuous web of waist containment member material 654, in which case the continuous web of waist containment member material 654 can be cut at the perforations by a further separating force at a rotating module 602, which is described further below. Cutting the continuous web of waist containment member material 654 can provide a waist containment member 54 with a proximal portion 76, an intermediate portion 77, a distal portion 78, a first longitudinal side edge 72, a second longitudinal side edge 74, an upper lateral edge 75, and a lower lateral edge 88 as illustrated in FIG. 9.

In some embodiments where an absorbent article 10 is manufactured in a machine direction process, the method 610 can include rotating the waist containment member 54 about 90 degrees after cutting the waist containment member 54 from the continuous web of waist containment member material 654. For example, in a preferred embodiment, a rotating module 602 can rotate the waist containment member 54. The general construction and operation of such a rotating module 602 is well known and is exemplified by U.S. Pat. Nos. 5,716,478 and 5,759,340 issued to Boothe et al. and U.S. Pat. No. 6,139,004 issued to Couillard et al., each of which is incorporated herein by reference in its entirety to the extent not inconsistent herewith. The rotating module 602 can include a plurality of transfer arms 604 (twelve transfer arms 604 are shown in FIG. 8) and a plurality of transfer pucks 606 (twelve transfer pucks 606 are shown in FIG. 8). The rotating module 602 can include a rotating means 607, such as a shaft 607a that can be directly or indirectly driven by a drive motor or other suitable means (not shown) as is conventionally used for such equipment. Thus, the rotation shaft 607a can propel the transfer arms 604 about an axis such that the transfer pucks 606 can transfer the waist containment members 54 from the anvil roll 695 to the chassis 11 (e.g., chassis web 611). If the knife roll 693 and anvil roll 695 are configured to perforate the continuous web of waist containment member material 654, the rotating module 602 can be configured to cut the continuous web of waist containment member material 654 at the perforations made by the knife roll 693 by applying a force to the continuous web of waist containment member material 654 when a transfer puck 606 picks up the continuous web of waist containment member material 654 and begins to transfer the continuous web of waist containment member material 654 at a faster speed than the anvil roll 695.

Each of the transfer pucks 606 can be coupled to a respective transfer arm 604. The transfer pucks 606 can be equipped with conventional vacuum assist or other means (not shown) to allow the transfer pucks 606 to pick up the waist containment members 54 (or continuous web of waist containment member material 654) from the knife roll 693 and the anvil roll 695. Each of the transfer pucks 606 is equipped with conventional means to pivot about the longitudinal axis of the respective transfer arm 604 so that each of the transfer pucks 606 are rotatable or pivotable between a first position when the transfer pucks 606 first receive the waist containment member 54 (or the continuous web of waist containment member material 654), such as shown by transfer puck 606a in FIG. 8, and a second position where the transfer pucks 606 transfer the waist containment member 54 to the chassis 11 (e.g., the chassis web 611), such as shown by transfer puck 606b. The transfer pucks 606 can rotate 90° from the first position (such as shown by transfer puck 606a) to the second position (such as shown by transfer puck 606b).

As illustrated in FIGS. 8 and 9, the waist containment member 54 is rotated about 90° by the rotating module 602 prior to bonding the waist containment member 54 to the chassis 11 (e.g., chassis web 611) to form containment member 54 on the absorbent article 10. It is contemplated, however, that in some embodiments no rotation of the waist containment member 54 is necessary. For example, if a cross-direction manufacturing process is utilized to provide an absorbent article, such as the absorbent article 110 of FIGS. 6 and 7 as discussed herein, then no rotation of the waist containment member 54 may be included in method 610.

The method 610 can also include bonding the waist containment member 54 to the chassis 11 (e.g., chassis web 611). The waist containment member 54 can be bonded to the chassis 11 (e.g., chassis web 611) by the adhesive 680 applied to the portion 654b of the continuous web of waist containment member material 654. The waist containment member 54 can also be bonded to the chassis 11 (e.g., chassis web 611) by the intermittent adhesives 681a, 681b and intermittent adhesive 683, which form the longitudinal tack-down regions 84a, 84b and the lateral tack-down regions 83a, 83b, as discussed above. The waist containment member 54 can be bonded to the body facing surface 19 of the chassis 11 (e.g., chassis web 311). In some embodiments, the waist containment member 54 can be bonded to the body facing surface 45 of the absorbent assembly 44 (e.g., the body facing surface 645 of the absorbent assembly web 644). As discussed above, the distal portion 78 of the waist containment member 54 can be bonded to the body facing surface 19 of the chassis 11 to provide a first lateral tack-down region 83a near the first longitudinal side edge 72 and a second lateral tack-down region 83b near the second longitudinal side edge 74 of the waist containment member 54 (e.g., with adhesive 683). The distal portion 78 of the waist containment member 54 can be bonded to the body facing surface 19 of the chassis 11 such that the first and second lateral tack-down regions 83a, 83b are at least about 3.0 mm away from the lower lateral edge 88 of the waist containment member 54, when the absorbent article 10 is in the stretched, laid-flat configuration. Of course, the positioning of the adhesive 683 can be adjusted with respect to the folded edge 679b of the continuous web of waist containment member material 654 such that the first and second lateral tack-down regions 83a, 83b are disposed more than about 3.0 mm away from the lower lateral edge 88 of the waist containment member 54, as discussed above.

The adhesive 683 can be applied to the continuous web of the waist containment member material 654 such that the spacing between consecutive adhesives 683 will form lateral tack-down regions 83a, 83b that bond the distal portion 78 of the waist containment member 54 to the body facing surface 19 of the chassis 11 from the first longitudinal side edge 72 of the waist containment member 54 to at least the proximal end 64a of the base portion 64 of the first containment flap 50 and will bond the distal portion 78 of the waist containment member 54 to the body facing surface 19 of the chassis 11 from the second longitudinal side edge 74 of the waist containment member 54 to at least the proximal end 64a of the base portion 64 of the second containment flap 52. More preferably, the adhesive 683 can be spaced such that the spacing between consecutive adhesives 683 will form lateral tack-down regions 83a, 83b that bond the distal portion 78 of the waist containment member 54 to the body facing surface 19 of the chassis 11 from the first longitudinal side edge 72 of the waist containment member 54 to the projection portion 66 of the first containment flap 50 and will bond the distal portion 78 of the waist containment member 54 to the body facing surface 19 of the chassis 11 from the second longitudinal side edge 74 of the waist containment member 54 to the projection portion 66 of the second containment flap 52.

If the chassis 11 is provided in the form of a chassis web 611, the method 610 can also include cutting the chassis web 611 to form individual absorbent articles. In one embodiment, cutting the chassis web 611 can be done with a cutoff module (not shown) as is known in the art.

EMBODIMENTS

Embodiment 1

An absorbent article including a front waist region, a rear waist region, a crotch region, a longitudinal axis and a lateral axis, the absorbent article comprising: a chassis including an absorbent body, the chassis including a body facing surface and a garment facing surface; a waist containment member disposed on the body facing surface of the chassis, the waist containment member comprising: a first longitudinal side edge and a second longitudinal side edge, the first longitudinal side edge being disposed on a first side of the longitudinal axis and the second longitudinal edge being disposed on a second side of the longitudinal axis; an upper lateral edge and a lower lateral edge, the first longitudinal side edge, the second longitudinal side edge, the upper lateral edge and the lower lateral edge of the waist containment member being defined when the absorbent article is in a stretched laid-flat configuration; a proximal portion, the proximal portion being coupled to the body facing surface of the chassis; a distal portion; and an intermediate portion, the intermediate portion being disposed between the proximal portion and the distal portion, the intermediate portion being free to move independent of the proximal portion and the distal portion and free to move independent of the body facing surface of the chassis to provide a containment pocket for containing body exudates; the distal portion being disposed underneath the intermediate portion when the absorbent article is in the stretched laid-flat configuration.

Embodiment 2

The absorbent article of embodiment 1, further comprising: a pair of containment flaps including a first containment flap and a second containment flap, the first containment flap being on the first side of the longitudinal axis and the second containment flap being on the second side of the longitudinal axis, the first and second containment flap each comprising: a base portion including a proximal end and a distal end; and a projection portion configured to extend away from the body facing surface of the chassis in at least the crotch region when the absorbent article is in a relaxed configuration.

Embodiment 3

The absorbent article of embodiment 2, wherein the waist containment member further comprises a first lateral tack-down region and a second lateral tack-down region, the first lateral tack-down region comprising the distal portion of the waist containment member on the first side of the longitudinal axis being coupled to the body facing surface of the chassis from the first longitudinal side edge to at least the proximal end of the base portion of the first containment flap and the second lateral tack-down region comprising the distal portion of the waist containment member on the second side of the longitudinal axis being coupled to the body facing surface of the chassis from the second longitudinal side edge to at least the proximal end of the base portion of the second containment flap.

Embodiment 4

The absorbent article of any one of embodiments 2 or 3, wherein the distal portion of the waist containment member is coupled to the base portion of the first and second containment flaps.

Embodiment 5

The absorbent article of embodiment 3, wherein the first lateral tack-down region and the second lateral tack-down region of the waist containment member are each disposed at least 3.0 mm away from the lower lateral edge of the waist containment member when the absorbent article is in the stretched laid-flat configuration.

Embodiment 6

The absorbent article of any one of the preceding embodiments, wherein the waist containment member further comprises at least one elastic member in the intermediate portion of the waist containment member.

Embodiment 7

The absorbent article of embodiment 6, wherein the waist containment member further comprises at least one elastic member in the distal portion of the waist containment member.

Embodiment 8

The absorbent article of any one of the preceding embodiments, wherein the waist containment member is a single component and further comprises a first fold between the proximal portion and the intermediate portion defining the upper lateral edge of the waist containment member, and a second fold in the intermediate portion defining the lower lateral edge of the waist containment member.

Embodiment 9

The absorbent article of any one of the preceding embodiments, wherein the intermediate portion is thicker than the proximal portion of the waist containment member.

Embodiment 10

An absorbent article including a front waist region, a rear waist region, a crotch region, a longitudinal axis and a lateral axis, the absorbent article comprising: a chassis including an absorbent body, the chassis including a body facing surface and a garment facing surface; a waist containment member disposed on the body facing surface of the chassis, the waist containment member comprising: a first longitudinal side edge and a second longitudinal side edge, the first longitudinal side edge being disposed on a first side of the longitudinal axis and the second longitudinal edge being disposed on a second side of the longitudinal axis; an upper lateral edge and a lower lateral edge, the first longitudinal side edge, the second longitudinal side edge, the upper lateral edge and the lower lateral edge of the waist containment member being defined when the absorbent article is in a stretched laid-flat configuration; a proximal portion, the proximal portion being coupled to the body facing surface of the chassis; a distal portion; and a first lateral tack-down region and a second lateral tack-down region, the first lateral tack-down region including the distal portion of the waist containment member on the first side of the longitudinal axis being coupled to the body facing surface of the chassis from the first longitudinal side edge in a lateral direction towards the proximal end of the base portion of the first containment flap and the second lateral tack-down region including the distal portion of the waist containment member on the second side of the longitudinal axis being coupled to the body facing surface of the chassis from the second longitudinal side edge in a lateral direction towards the proximal end of the base portion of the second containment flap, wherein the waist containment member is gathered in the longitudinal direction such that the waist containment member can extend away from the body facing surface of the chassis to provide a containment pocket for containing exudates between the first lateral tack-down region and the upper lateral edge of the waist containment member and between the second lateral tack-down region and the upper lateral edge of the waist containment member.

Embodiment 11

The absorbent article of embodiment 10, wherein the waist containment member further comprises: a first longitudinal tack-down region and a second longitudinal tack-down region, the first longitudinal tack-down region being disposed near the first longitudinal side edge of the waist containment member and the second longitudinal tack-down region being disposed near the second longitudinal side edge of the waist containment member.

Embodiment 12

The absorbent article of embodiment 10 or embodiment 11, further comprising: a pair of containment flaps including a first containment flap and a second containment flap, the first containment flap being on the first side of the longitudinal axis and the second containment flap being on the second side of the longitudinal axis, the first and second containment flap each comprising: a base portion including a proximal end and a distal end; and a projection portion configured to extend away from the body facing surface of the chassis in at least the crotch region when the absorbent article is in a relaxed configuration.

Embodiment 13

The absorbent article of embodiment 12, wherein the first lateral tack-down region extends from the first longitudinal side edge of the waist containment member to at least the proximal end of the base portion of the first containment flap and the second lateral tack-down region extends from the second longitudinal side edge of the waist containment member to at least the proximal end of the base portion of the second containment flap.

Embodiment 14

The absorbent article of any one of embodiments 10-13, wherein the distal portion of the waist containment member is gathered in the longitudinal direction to provide the void volume.

Embodiment 15

The absorbent article of any one of embodiments 10-14, wherein the waist containment member further comprises an intermediate portion, the intermediate portion being disposed between the proximal portion and the distal portion, the intermediate portion being free to move independent of the proximal portion and the distal portion; the distal portion being gathered in the longitudinal direction by being disposed underneath the intermediate portion when the absorbent article is in the stretched laid-flat configuration.

Embodiment 16

The absorbent article of embodiment 15, wherein the first lateral tack-down and the second lateral tack-down are each disposed at least 3.0 mm away from the lower lateral edge of the waist containment member to provide the void volume when the absorbent article is in the stretched laid-flat configuration.

Embodiment 17

A method of manufacturing an absorbent article, the absorbent article including a front waist region, a rear waist region, a crotch region, a longitudinal axis and a lateral axis, the method comprising: providing a chassis including a body facing surface, the chassis comprising an absorbent assembly including a bodyside liner, an outer cover, and an absorbent body disposed between the bodyside liner and the outer cover, the absorbent assembly including a body facing surface; providing a continuous web of waist containment member material; folding at least a first portion of the continuous web of waist containment member material upon itself to provide a folded edge; cutting the continuous web of waist containment member material to provide a waist containment member including a proximal portion, an intermediate portion, a distal portion, a first longitudinal side edge, a second longitudinal side edge, an upper lateral edge, and a lower lateral edge, wherein the folded edge provides the distal portion to be folded against the intermediate portion and the folded edge defines the lower lateral edge of the waist containment member, the intermediate portion being disposed between the proximal portion and the distal portion; bonding the proximal portion of the waist containment member to the body facing surface of the chassis; bonding the distal portion of the waist containment member to the body facing surface of the chassis to provide a first lateral tack-down region near the first longitudinal side edge of the waist containment member and a second lateral tack-down region near the second longitudinal side edge of the waist containment member, the first lateral tack-down region and the second lateral tack-down region being formed such that the first lateral tack-down region and the second lateral tack-down region of the waist containment member are disposed away from the lower lateral edge of the waist containment member when the absorbent article is in the stretched laid-flat configuration.

Embodiment 18

The method of manufacturing an absorbent article of embodiment 17, further comprising bonding the waist containment member to the body facing surface of the chassis to provide a first longitudinal tack-down region near the first longitudinal side edge and a second longitudinal tack-down region near the second longitudinal side edge.

Embodiment 19

The method of manufacturing an absorbent article of embodiment 17 or embodiment 18, further comprising: providing a pair of containment flaps including a first containment flap and a second containment flap, the first containment flap and the second containment flap each including a base portion and a projection portion; and bonding the base portion of each of the first and the second containment flaps to the body facing surface of the absorbent assembly, the base portion of each of the first and the second containment flaps each including a proximal end and a distal end.

Embodiment 20

The method of manufacturing an absorbent article of embodiment 19, wherein the first lateral tack-down region comprises the distal portion of the waist containment member being coupled to the body facing surface of the chassis from the first longitudinal side edge to at least the proximal end of the base portion of the first containment flap and the second lateral tack-down region comprises the distal portion of the waist containment member on the second side of the longitudinal axis being coupled to the body facing surface of the chassis from the second longitudinal side edge to at least the proximal end of the base portion of the second containment flap.

Embodiment 21

The method of manufacturing an absorbent article of embodiment 17, further comprising: folding at least a second portion of the continuous web of waist containment member material upon itself to provide a second folded edge, the second folded edge defining the upper lateral edge of the waist containment member when the absorbent article is in the stretched laid-flat configuration.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing an absorbent article, the absorbent article including a front waist region, a rear waist region, a crotch region, a longitudinal axis and a lateral axis, the method comprising:
    providing a chassis including a body facing surface, the chassis comprising an absorbent assembly including a bodyside liner, an outer cover, and an absorbent body disposed between the bodyside liner and the outer cover, the absorbent assembly including a body facing surface;
    providing a continuous web of waist containment member material;
    folding at least a first portion of the continuous web of waist containment member material upon itself to provide a folded edge;

cutting the continuous web of waist containment member material to provide a waist containment member including a proximal portion, an intermediate portion, a distal portion, a first longitudinal side edge, a second longitudinal side edge, an upper lateral edge, and a lower lateral edge, wherein the folded edge provides the distal portion to be folded against the intermediate portion and the folded edge defines the lower lateral edge of the waist containment member, the intermediate portion being disposed between the proximal portion and the distal portion;

bonding the proximal portion of the waist containment member to the body facing surface of the chassis;

bonding the distal portion of the waist containment member to the body facing surface of the chassis to provide a first lateral tack-down region near the first longitudinal side edge of the waist containment member and a second lateral tack-down region near the second longitudinal side edge of the waist containment member, the first lateral tack-down region and the second lateral tack-down region being formed such that the first lateral tack-down region and the second lateral tack-down region of the waist containment member are disposed away from the lower lateral edge of the waist containment member when the absorbent article is in a stretched laid-flat configuration.

2. The method of manufacturing an absorbent article of claim 1, further comprising bonding the waist containment member to the body facing surface of the chassis to provide a first longitudinal tackdown region near the first longitudinal side edge and a second longitudinal tack-down region near the second longitudinal side edge.

3. The method of manufacturing an absorbent article of claim 1, further comprising:
providing a pair of containment flaps including a first containment flap and a second containment flap, the first containment flap and the second containment flap each including a base portion and a projection portion; and
bonding the base portion of each of the first and the second containment flaps to the body facing surface of the absorbent assembly, the base portion of each of the first and the second containment flaps each including a proximal end and a distal end.

4. The method of manufacturing an absorbent article of claim 3, wherein the first lateral tack-down region comprises the distal portion of the waist containment member being coupled to the body facing surface of the chassis from the first longitudinal side edge to at least the proximal end of the base portion of the first containment flap and the second lateral tack-down region comprises the distal portion of the waist containment member on the second side of the longitudinal axis being coupled to the body facing surface of the chassis from the second longitudinal side edge to at least the proximal end of the base portion of the second containment flap.

5. The method of manufacturing an absorbent article of claim 1, further comprising folding at least a second portion of the continuous web of waist containment member material upon itself to provide a second folded edge, the second folded edge defining the upper lateral edge of the waist containment member when the absorbent article is in the stretched laid-flat configuration.

6. The method of claim 1, wherein bonding the distal portion of the waist containment member to the body facing surface of the chassis further comprises bonding the distal portion of the waist containment member to the body facing surface of the chassis such that the intermediate portion is free to move independent of the proximal portion and the distal portion and free to move independent of the body facing surface of the chassis to provide a containment pocket for containing body exudates.

7. The method of claim 1, wherein bonding the distal portion of the waist containment member to the body facing surface of the chassis further comprises bonding the distal portion of the waist containment member to the body facing surface of the chassis such that the distal portion is disposed underneath the intermediate portion when the absorbent article is in the stretched laid-flat configuration.

8. The method of claim 1, further comprises forming a fold between the proximal portion and the intermediate portion which defines the upper lateral edge of the waist containment member.

* * * * *